(12) United States Patent
Davies et al.

(10) Patent No.: US 7,973,162 B2
(45) Date of Patent: Jul. 5, 2011

(54) MODULATORS OF MUSCARINIC RECEPTORS

(75) Inventors: Robert J. Davies, Watertown, MA (US); Jinwang Xu, Framingham, MA (US); Rieko Arimoto, Tewksbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 146 days.

(21) Appl. No.: 12/287,055

(22) Filed: Oct. 3, 2008

(65) Prior Publication Data

US 2009/0099222 A1    Apr. 16, 2009

Related U.S. Application Data

(60) Provisional application No. 60/977,220, filed on Oct. 3, 2007.

(51) Int. Cl.
A61K 31/438 (2006.01)
C07D 491/10 (2006.01)
C07D 487/10 (2006.01)

(52) U.S. Cl. .......................... 546/20; 514/290
(58) Field of Classification Search ............ 546/20; 514/290
See application file for complete search history.

(56) References Cited

U.S. PATENT DOCUMENTS

| | | |
|---|---|---|
| 3,654,287 A | 4/1972 | Dykstra |
| 3,666,764 A | 5/1972 | Campbell et al. |
| 3,959,475 A | 5/1976 | Bauer et al. |
| 3,962,259 A | 6/1976 | Bauer et al. |
| 4,233,307 A | 11/1980 | Ono et al. |
| 4,349,549 A | 9/1982 | Roskowski et al. |
| 4,558,049 A | 12/1985 | Bernardi et al. |
| 4,612,121 A | 9/1986 | Hermansson |
| 5,091,387 A | 2/1992 | Evans et al. |
| 5,219,860 A | 6/1993 | Chambers et al. |
| 5,324,733 A | 6/1994 | Billington |
| 5,457,207 A | 10/1995 | Efange et al. |
| 5,536,716 A | 7/1996 | Chen et al. |
| 5,576,321 A | 11/1996 | Krushinski, Jr. et al. |
| 5,578,593 A | 11/1996 | Chen et al. |
| 5,614,523 A | 3/1997 | Audia et al. |
| 5,627,196 A | 5/1997 | Audia et al. |
| 5,652,235 A | 7/1997 | Chen et al. |
| 5,658,921 A | 8/1997 | Perregaard et al. |
| 5,665,725 A | 9/1997 | Moltzen et al. |
| 5,693,643 A | 12/1997 | Gilbert et al. |
| 5,741,789 A | 4/1998 | Hibschman et al. |
| 5,789,402 A | 8/1998 | Audia et al. |
| 5,817,679 A | 10/1998 | Shen et al. |
| 5,885,999 A | 3/1999 | Elliott et al. |
| 6,013,652 A | 1/2000 | Maccoss et al. |
| 6,130,217 A | 10/2000 | Arnold et al. |
| 6,166,040 A | 12/2000 | Fairhurst et al. |
| 6,294,534 B1 | 9/2001 | Nargund et al. |
| 6,316,437 B1 | 11/2001 | Hoffman |
| 6,326,375 B1 | 12/2001 | Fukami et al. |
| 6,436,962 B1 | 8/2002 | Hoffman et al. |
| 6,566,367 B2 | 5/2003 | Bakthavatchalam et al. |
| 6,713,487 B2 | 3/2004 | Yu et al. |
| 6,720,324 B2 | 4/2004 | Marzabadi et al. |
| 6,828,440 B2 | 12/2004 | Goehring et al. |
| 6,869,960 B2 | 3/2005 | Ito et al. |
| 6,943,199 B2 | 9/2005 | DeLombaert et al. |
| 7,045,527 B2 | 5/2006 | Chen et al. |
| 7,205,417 B2 | 4/2007 | Fukami et al. |
| 7,279,471 B2 | 10/2007 | Mueller et al. |
| 7,351,706 B2 | 4/2008 | Bissantz et al. |
| 7,491,715 B2 | 2/2009 | Ek et al. |
| 2002/0188124 A1 | 12/2002 | Fukami et al. |
| 2003/0036652 A1 | 2/2003 | Bakthavatchalam et al. |
| 2003/0158219 A1 | 8/2003 | Ito et al. |
| 2004/0054177 A1 | 3/2004 | Otake et al. |
| 2004/0072847 A1 | 4/2004 | Bakthavatchalam et al. |
| 2004/0122074 A1 | 6/2004 | Dow et al. |
| 2004/0142956 A1 | 7/2004 | Chen et al. |
| 2004/0204397 A1 | 10/2004 | Chaturvedula et al. |
| 2005/0033048 A1 | 2/2005 | Bakthavatchalam et al. |
| 2005/0143372 A1 | 6/2005 | Ghosh et al. |
| 2005/0153998 A1 | 7/2005 | Ito et al. |
| 2005/0176703 A1 | 8/2005 | Gabriel et al. |
| 2005/0215576 A1 | 9/2005 | Degnan et al. |
| 2005/0261332 A1 | 11/2005 | Distefano et al. |
| 2006/0019962 A1 | 1/2006 | Makings et al. |
| 2006/0040964 A1 | 2/2006 | Bakthavatchalam et al. |
| 2006/0058778 A1 | 3/2006 | Villacampa et al. |
| 2006/0106045 A1 | 5/2006 | Hughes et al. |
| 2006/0111380 A1 | 5/2006 | Otake et al. |
| 2006/0173027 A1 | 8/2006 | Marzabadi et al. |

(Continued)

FOREIGN PATENT DOCUMENTS

CN          1535967          10/2004

(Continued)

OTHER PUBLICATIONS

English abstract , Caplus, DN 36:35100, 1941, RN # 1087702-80-4P.*
Abdel-Magid, A., "Reductive Amination of Aldehydes and Ketones with Sodium Triacetoxyborohydride. Studies on Direct and Indirect Reductive Amination Procedures1", J. Org. Chem., 61 (1996), pp. 3849-3862.
Bignan, G., "Preparation of 3-Spirocyclic Indolin-2-ones as Ligands for the ORL-1 Receptor", Bioorganic and Medicinal Chem. Lett, 15 (2005), pp. 5022-5026.
Butera, J., "Recent Approaches to the Treatment of Urinary Incontinence: A Survey of Patent Activity from 1995 to 1998", Expert Opinion on Therapeutic Patents, 8(8) (1998), pp. 1017-1035.
Bymaster, F., "Xanomeline: A Selective Muscarinic Agonist for the Treatment of Alzheimer's Disease", Drug Development Research, 40 (1997), pp. 158-170.
Caufield, M.P., "International Union of Pharmacology. XVII. Classification of Muscarinic Acetylcholine Receptors", Pharmacol. Rev., 50 (1998), pp. 279-290.
Caufield, M.P., "Muscarinic Receptors-Characterization, Coupling and function", Pharmac. Ther., vol. 58 (1993), pp. 319-379.
Chambers, M., "Spiropiperidines as High-Affinity, Selective σ Ligands", J. Med. Chem., 35(11), (1992), pp. 2033-2039.

(Continued)

*Primary Examiner* — Rita J Desai
(74) *Attorney, Agent, or Firm* — Honigman Miller Schwartz and Cohn LLP; Christopher C. Forbes; Jonathan P. O'Brien

(57) ABSTRACT

The present invention relates to modulators of muscarinic receptors. The present invention also provides compositions comprising such modulators, and methods therewith for treating muscarinic receptor mediated diseases.

25 Claims, No Drawings

U.S. PATENT DOCUMENTS

| | | | |
|---|---|---|---|
| 2006/0183904 A1 | 8/2006 | Guo et al. |
| 2006/0211722 A1 | 9/2006 | Jiao et al. |
| 2006/0217372 A1 | 9/2006 | Blanco-Pillado et al. |
| 2006/0270673 A1 | 11/2006 | Duggan et al. |
| 2007/0043023 A1 | 2/2007 | Makings et al. |
| 2007/0149502 A1 | 6/2007 | Chaturvedula et al. |
| 2007/0213315 A1 | 9/2007 | Davies et al. |
| 2007/0254903 A1 | 11/2007 | Boatman et al. |
| 2008/0003302 A1 | 1/2008 | Davenport et al. |
| 2008/0171753 A1 | 7/2008 | Jitsuoka et al. |

FOREIGN PATENT DOCUMENTS

| | | |
|---|---|---|
| EP | 0070171 | 1/1983 |
| EP | 0 414 289 | 2/1991 |
| EP | 0414289 | 2/1991 |
| EP | 0444945 | 9/1991 |
| EP | 0486280 | 5/1992 |
| GB | 1575800 | 10/1980 |
| GB | 2308064 | 6/1997 |
| JP | 59059685 | 4/1984 |
| JP | 2001/278886 | 10/2001 |
| JP | 2002/316987 | 10/2002 |
| WO | WO 94/22846 | 10/1994 |
| WO | WO 95/11029 | 4/1995 |
| WO | WO 95/14025 | 5/1995 |
| WO | WO 95/28389 | 10/1995 |
| WO | WO 97/41878 | 11/1997 |
| WO | WO 97/41879 | 11/1997 |
| WO | WO 99/06434 | 2/1999 |
| WO | WO 99/32489 | 7/1999 |
| WO | WO 00/06146 | 2/2000 |
| WO | WO 00/06153 | 2/2000 |
| WO | WO 00/06545 | 2/2000 |
| WO | WO 00/38720 | 7/2000 |
| WO | WO 01/02386 | 1/2001 |
| WO | WO 01/22919 | 4/2001 |
| WO | WO 01/29027 | 4/2001 |
| WO | WO 01/45707 | 6/2001 |
| WO | WO 01/64213 | 9/2001 |
| WO | WO 02/094825 | 11/2002 |
| WO | WO 03/095427 | 11/2003 |
| WO | WO 2004/010942 | 2/2004 |
| WO | WO 2004/010943 | 2/2004 |
| WO | WO 2004/011427 | 2/2004 |
| WO | WO 2005/065779 | 7/2005 |
| WO | WO 2006/001958 | 1/2006 |
| WO | WO 2006/023852 | 3/2006 |
| WO | WO 2007/100664 | 9/2007 |
| WO | WO 2008/005295 | 1/2008 |

OTHER PUBLICATIONS

Cheng, Y., "Solid Phase Synthesis of Spiroindoline", Tet. Lett., 38 (1997), pp. 1497-1500.

Chiaverelli, S., "ricerche nella serle della 4-finiipiperidina. Nota v. Derivati della 4,4'-spiro-(1 metilpiperidin)-1,2,3,4,-tetraidroisochinolina", Gazzetta Chimica Italiana, 90, 189 (1960), CN1535967.

Custers, F., "Vesamicol and Some of its Derivatives: Questionable Ligands for Selectively Labelling Acetylcholine Transporters in Rat Brain", Eur. Jour. of Pharm., 338 (1997), pp. 177-183.

deLaszlo, S., "A Nonpeptidic Agonist Ligand of the Human C5A Receptor: Synthesis, Binding Affinity Optimization and functional Characterization", Bioorganic and Medicinal Chem. Lett., 7(2) (1997), pp. 213-218.

Dhar, T.G., "Design and Synthesis of Novel α1a Adrenoceptor-Selective Antagonists. 2. Approaches to Eliminate Opiod Agonist Metabolites via Modification of Linker and 4-Methoxycarbonyl-4-phenylpiperidine Moiety1.2", J. Med. Chem., 42 (1999), pp. 4778-4793.

Efange, S., "(+)-p-([18F]Fluorobenzyl)Spirotrozamicol {(+)-[18F]Spiro-FBT}: Synthesis and Biological Evaluation of a High-Affinity Ligand for the Vesicular Acetylcholine Transporter (VAChT)", Nuclear Medicine and Biology, vol. 26 (1999), pp. 189-192.

Efange, S., "Comparative Tissue Distribution of Conformationally Restricted Radioiodinated Vesamicol Receptor Ligands", Nuclear Medicine and Biology, 22(4) (1995), pp. 437-444.

Efange, S., "Molecular Determinants of Selectivity at the Vesamicol Receptor", Biochem. Phar., 49(6) (1995), pp. 791-797.

Efange, S., "N-Hydroxyalkyl Derivatives of 3β-Phenyltropane and Methylspiro[1H-indoline-3,4'-piperidine]: Vesamicol Analogues with Affinity or Monoamine Transporters", J. Med. Chem., 40 (1997), pp. 3905-3914.

Efange, S., "Spirovesamicols: Conformationally Restricted Analogs of 2-(4-Phenylpiperidino)cyclohexanol (Vesamicol, AH5183) as Potential Modulators of Presynaptic Cholinergic Function", J. Med. Chem., 37 (1994), pp. 2574-2582.

Evans, B., "Orally Active, Nonpeptide Oxytocin Antagonists", J. Med. Chem., 35(21) (1992), pp. 3919-3927.

Felder, C., "Therapeutic Opportunities for Muscarinic Receptors in the Central Nervous System", J. Med. Chem., 43 (23) (2000), pp. 4333-4353.

Freireich, "Quantitative Comparison of Toxicity of Anticancer Agengs in Mouse, Rat, Hamster, Dog, Monkey and Man,", Cancer Chemother. Rep., 50, 219 (1966).

Hulme, E.C., "Muscarinic Receptor Subtypes", Annu. Rev. Pharmacol. Toxicol., 30 (1990), pp. 633-673.

Kim, D., "Discovery of Human CCR5 Antagonists Containing Hydantoins for the Treatment of HIV-1 Infection", Bioorganic and Medicinal Chem. Lett., 11 (2001), pp. 3099-3102.

Maligres, P.E., "Synthesis of the Orally Active Spiroindoline-Based Growth Hormone Secretagogue, MK-677", Tetrahedron, 53 (1997), pp. 10983-10992.

Malmstrom, R., "Pharmacology of H 394/84, a dihydropyridine neuropeptide Y Y1 Receptor Antagonist, in Vivo", Eur. Jour. of Pharm., 418 (2001), pp. 95-104.

Matier, W., "Novel Cyclizations and Ring-Opening Reactions of 3-Phenylindene Derivatives", J. Org. Chem., vol. 36, No. 5 (1971), pp. 650-654.

Moltzen, E., "σ Ligands with Subnanomolar Affinity and Preference for the σ2 Binding Site. 2. Spiro-Joined Benzofuran, Isobenzofuran and Benzopyran Piperidines", J. Med. Chem., 38 (1995), pp. 2009-2017.

Morrow, D., "Synthesis of Some New 17-Spiro-Substituted Steroids", J. Med. Chem., 10(2) (1967), pp. 133-138.

Nargund, R., "Peptidomimetic Growth Hormone Secretagogues: Synthesis and Biological Activities of Analogs Varied at the Indole Nucleus of the Prototypical Spiropiperidine L-162,752", Bioorganic and Medicinal Chem. Lett., vol. 6, No. 14 (1996), pp. 1731-1736.

Nargund, R., "Synthesis and Biological Activities of Camphor-Based Non-Peptide Growth Hormone Secretagogues", Bioorganic and Medicinal Chem. Lett., vol. 6, No. 11 (1996), pp. 1265-1270.

Oprea, T., "Is there a Difference Between Leads and Drugs? A Historical Perspective", J. Chem. Inf. Comput. Sci., 41 (2001), pp. 1308-1315.

Pasternak, A., "Potent, Orally Bioavailable Somatostatin Agonists: Good Absorption Achieved by Urea Backbone Cyclization", Bioorganic and Medicinal Chem. Lett., 9 (1999), pp. 491-496.

Patchett, A.A., "The Synthesis of 17β-Amino-17 α-(2'-carboxyethyl)androstane Lacatama1", J. Org. Chem, 27 (1962), pp. 3822-3828.

Pettibone, D.J., "Identification of an Orally Active, Nonpeptidyl Oxytocin Antagonist", Journal of Pharm. and Experimental Therap., 264(1) (1993), pp. 308-314.

Reimann, E., "Synthese und pharmakologische Prüfung Homologer und hydroxylierter 3,4-Dihydro-1'-methylspiro [naphthalin-(2H),4'-piperidine]", Archiv. Der. Pharmazie, VCH Verlagsgesellschaft MBH, Weinheim, DE, 323 (1990), pp. 35-39.

Rubin, "Novel Medications for Asthma: A Look into the Future", Exper. Opinion on Investigational Drugs 16(6) (2007), pp. 889-897.

Takemoto, T., "Asymmetric Synthesis of Enantiomerically Pure Spiro[((2S)-hydroxy)indane-1,4'-piperidine]", Tetrahedron Asymmetry, 10 (1999), pp. 1787-1793.

Tata, J., "The Synthesis and Activity of Spiroindane Growth Hormone Secretagogues", Bioorganic and Medicinal Chem. Lett, 7(6) (1997), pp. 663-668.

Williams, P., "1-(((7,7-Dimethyl-2(S)-(2(S)-amino-4-(methylsulfonyl)butyramido)bicyclo[2.2.1]-heptan-1(S)-yl)methyl) sulfonyl)-4-2(2-methylphenyl)piperazine (L-368,899): An Orally Bioavailable, Non-Peptide Oxytocin Antagonist with Potential Utility for Managing Preterm Labor", J. Med. Chem., 37 (1994), pp. 555-571.

Yang, L., "Potent 3-Spiropiperidine Growth Hormone Secretagogues", Bioorganic and Medicinal Chem. Lett., 8(1) (1998), pp. 107-112.

Yang, L., "The Design and Synthesis of Non-Peptide Somatostatin Receptor Agonists", Proceedings of the American Peptide Symposium, 16th Minneapolis, MN, Jun. 26-Jul. 1, 1999, (2000), meeting date 1999, 250-252.

* cited by examiner

MODULATORS OF MUSCARINIC RECEPTORS

CROSS-REFERENCE TO RELATED APPLICATIONS

The present application claims priority under 35 U.S.C. §119 to U.S. Provisional Application No. 60/977,220, filed Oct. 3, 2007 and entitled "MODULATORS OF MUSCARINIC RECEPTORS," the entire contents of which is incorporated herein by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43(23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors—Characterization, Coupling, and Function," Pharmacol. Ther., 58, pp. 319-379 (1993); Caulfield, M. P. et al., International Union of Pharmacology. XVII. Classification of Muscarinic Acetylcholine Receptors," Pharmacol. Rev., 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating the activity of a muscarinic receptor (e.g., $M_1$, $M_2$, $M_3$, $M_4$, $M_5$, or combinations thereof) using compounds of formula I:

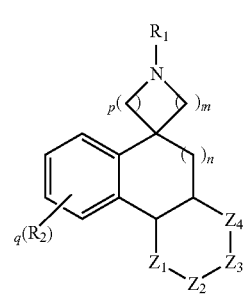

I or a pharmaceutically acceptable salt thereof, wherein $R_1$, $R_2$, $Z_1$, $Z_2$, $Z_3$, $Z_4$, n, m, p, and q are described below.

Another aspect of the present invention provides methods of treating or reducing the severity of a muscarinic receptor mediated disease in a mammal, comprising the step of administering to said mammal a compound as described above. In several embodiments, the muscarinic receptor is $M_4$. In others, the muscarinic receptor is $M_1$.

Another aspect of the present invention provides methods of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis associated with CNS disorders including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradycardia, gastric acid secretion, asthma, GI disturbances, and wound healing, wherein said method comprises the step of contacting said patient with a compound as described above.

Another aspect of the present invention provides pharmaceutical compositions comprising a compound described above and a pharmaceutical carrier.

DETAILED DESCRIPTION

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B.

and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)—N($R^X$)— or —N($R^X$)—C (O)— when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic) aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic) carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl) carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl) aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy) alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "carbocycle" or "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2] octyl, bicyclo[3.3.1]nonyl, bicyclo[3.3.2.]decyl, bicyclo [2.2.2]octyl, adamantyl, or ((aminocarbonyl)cycloalkyl) cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic) carbonylamino, (aryl)carbonylamino, (araliphatic)carbonylamino, (heterocycloaliphatic)carbonylamino, ((heterocycloaliphatic)aliphatic)carbonylamino, (heteroaryl) carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycle" or "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b] thiopheneyl, 2-oxa-bicyclo[2.2.2]octyl, 1-aza-bicyclo[2.2.2] octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (aralaphatic)oxy, (heteroaralphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (aralphatic)carbonylamino, (heterocycloaliphatic)carbonylamino, ((heterocycloaliphatic) aliphatic)carbonylamino, (heteroaryl)carbonylamino, or (heteroaralphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (aralphatic)carbonyl, (heterocycloaliphatic)carbonyl, ((heterocycloaliphatic)aliphatic) carbonyl, or (heteroaralphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizinyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (aralphatic)oxy; (heteroaralphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (aralphatic)carbonyl; (heterocycloaliphatic)carbonyl; ((heterocycloaliphatic)aliphatic)carbonyl; or (heteroaralphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl; and (haloalkyl)heteroaryl [e.g., trihaloalkylheteroaryl].

A "heteroaralphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicaliphatic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—$NR^XR^Y$ or —$NR^X$—CO—O—$R^Z$, wherein $R^X$ and $R^Y$ have been defined above and $R^Z$ can be aliphatic, aryl, aralphatic, heterocycloaliphatic, heteroaryl, or heteroaraliphatic.

As used herein, a "carboxy" group refers to —COOH, —$COOR^X$, —OC(O)H, —OC(O)$R^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —$S(O)_3$— when used internally.

As used herein, a "sulfamide" group refers to the structure —$NR^X$—$S(O)_2$—$NR^YR^Z$ when used terminally and —$NR^X$—$S(O)_2$—$NR^Y$— when used internally, wherein $R^X$, $R^Y$, and $R^Z$ have been defined above.

As used herein, a "sulfonamide" group refers to the structure —$S(O)_2$—$NR^XR^Y$ or —$NR^X$—$S(O)_2$—$R^Z$ when used terminally; or —$S(O)_2$—$NR^X$— or —$NR^X$—$S(O)_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include aliphatic-S—, cycloaliphatic-S—, aryl-S—, or the like.

As used herein a "sulfinyl" group refers to —S(O)—$R^X$ when used terminally and —S(O)— when used internally, wherein $R^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —$S(O)_2$—$R^X$ when used terminally and —$S(O)_2$— when used internally, wherein $R^X$ has been defined above. Exemplary sulfonyl groups include aliphatic-$S(O)_2$—, aryl-$S(O)_2$—, (cycloaliphatic(aliphatic))-$S(O)_2$—, cycloaliphatic-$S(O)_2$—, heterocycloaliphatic-$S(O)_2$—, heteroaryl-$S(O)_2$—, (cycloaliphatic(amido(aliphatic)))-$S(O)_2$— or the like.

As used herein, a "sulfoxy" group refers to —O—SO—$R^X$ or —SO—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —$P(O)(R^P)_2$, wherein $R^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure $(R^X)_2$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —$[CH_2]_v$—, where v is 1-12. A branched aliphatic chain is a straight aliphatic chain that is substituted with one or more aliphatic groups. A branched aliphatic chain has the structure —$[CQQ]_v$- where each Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, $Z_1$, $Z_2$, $Z_3$, $Z_4$, n, m, p, q, and other variables contained in formulae described herein encompass specific groups, such as alkyl and aryl. Unless otherwise noted, each of the specific groups for the variables $R_1$, $R_2$, $R_1$, $R_2$, $Z_1$, $Z_2$, $Z_3$, $Z_4$, n, m, p, q, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays, or as therapeutic agents.

II. Compounds

A. Generic Compounds

The present invention provides methods of modulating activity of a muscarinic receptor comprising the step of contacting said receptor with a compound of formula I:

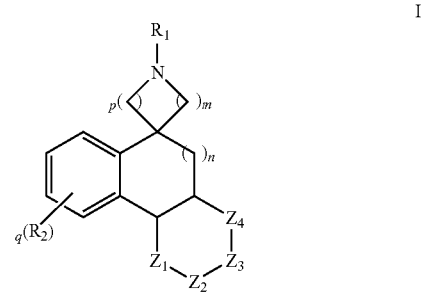

or a pharmaceutically acceptable salt thereof.

$R_1$ is —$Z^A R_4$, wherein $Z^A$ is independently a bond or an optionally substituted branched or straight chain $C_{1-12}$ aliphatic wherein up to 3 carbon units of $R_1$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$CO—, —S—, —S(O)—, —S(O)$_2$—, —NR$^A$—, —S(O)$_2$NR$^A$—, —NR$^A$SO$_2$—, or —NR$^A$S(O)$_2$NR$^A$. Each $R_4$ is independently $R^A$, halo, —OH, —NH$_2$, —NO$_2$, —CN, or —OCF$_3$. Each $R^A$ is independently a cycloaliphatic, heterocycloaliphatic, aryl, or heteroaryl, each of which is optionally substituted.

$R_2$ is —$Z^B R_5$, wherein each $Z^B$ is independently a bond or an optionally substituted branched or straight $C_{1-12}$ aliphatic chain wherein up to two carbon units of $Z^B$ are optionally and independently replaced by —CO—, —CS—, —CONR$^B$—, —CONR$^B$NR$^B$—, —CO$_2$—, —OCO—, —NR$^B$CO$_2$—, —O—, —NR$^B$CONR$^B$—, —OCONR$^B$—, —NR$^B$NR$^B$—, —NR$^B$CO—, —S—, —S(O)—, —S(O)$_2$—, —NR$^B$—, —S(O)$_2$NR$^B$—, —NR$^B$S(O)$_2$—, or —NR$^B$S(O)$_2$NR$^B$—. Each $R_5$ is independently $R^B$, halo, —OH, —CN, or —OCF$_3$. Each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

Each of $Z_1$, $Z_2$, $Z_3$, and $Z_4$ is independently a bond or —CR$_3$R'$_3$—, —NR$_3$—, or —O— wherein each $R_3$ and R'$_3$ is —$Z^C R_6$, wherein each $Z^C$ is independently a bond or an optionally substituted branched or straight $C_{1-12}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—. Each $R_6$ is independently $R^C$, halo, —OH, —CN, or —OCF$_3$. Each $R^C$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

Alternatively, $R_3$ and $R'_3$ together form an oxo group.

p is 0-3, m is 0-3, and p+m is 3 or 4.

n is 0 or 1.

q is 0-4.

B. Specific Compounds

1. Substituent $R_1$:

$R_1$ is —$Z^A R_4$, wherein $Z^A$ is independently a bond or an optionally substituted branched or straight $C_{1-12}$ aliphatic wherein up to 3 carbon units of $R_1$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$—, —OCONR$^A$—, —NR$^A$NR$^A$—, —NR$^A$CO—, —S—, —S(O)—, —S(O)$_2$—, —NR$^A$—, —S(O)$_2$NR$^A$—, —NR$^A$SO$_2$—, or —NR$^A$S(O)$_2$NR$^A$. Each $R_4$ is independently $R^A$, halo, —OH, —NH$_2$, —NO$_2$, —CN, or —OCF$_3$. Each $R^A$ is independently a cycloaliphatic, heterocycloaliphatic, aryl, or heteroaryl, each of which is optionally substituted.

In several embodiments, $R_1$ is a straight or branched $C_{1-6}$ aliphatic, wherein up to 3 carbon units of $R_1$ are optionally and independently replaced with —C(O)—, —S(O)$_2$—, —S—, —O—, or combinations thereof, and at least one of the carbon units of $R_1$ is substituted with a cycloaliphatic, a heterocycloaliphatic, an aryl, or a heteroaryl, each of which is optionally substituted.

In other embodiments, $R_1$ is —$Z^A R_4$, wherein $Z^A$ is —CH$_2$—, and $R_4$ is an optionally substituted cycloaliphatic or an optionally substituted heterocycloaliphatic. For example, $R_1$ is —$Z^A R_4$, wherein $Z^A$ is —CH$_2$—, and $R_4$ is an optionally substituted monocyclic cycloaliphatic or an optionally substituted bicyclic cycloaliphatic. In several examples, $R_1$ is —$Z^A R_4$, wherein $Z^A$ is —CH$_2$—, and $R_4$ is an optionally substituted 3-7 membered monocyclic cycloalkyl or cycloalkenyl, either of which is optionally substituted. For instance, $R_1$ is —$Z^A R_4$, wherein $Z^A$ is —CH$_2$—, and $R_4$ is an optionally substituted 3-7 membered optionally substituted monocyclic cycloalkyl. In other examples, $R_1$ is —$Z^A R_4$, wherein $Z^A$ is —CH$_2$—, and $R_4$ is cyclopropyl, cyclobutyl, cyclopentyl, cyclohexyl, or cycloheptyl, each of which is optionally substituted. In alternative examples, $R_1$ is —$Z^A R_4$, wherein $Z^A$ is —CH$_2$—, and $R_4$ is an unsubstituted cyclopropyl, cyclobutyl, cyclopentyl, cyclohexyl, or cycloheptyl.

In other embodiments, $R_1$ is —$Z^A R_4$, wherein $Z^A$ is —CH$_2$—, and $R_4$ is an optionally substituted bicyclic cycloaliphatic. For example, $R_1$ is —$Z^A R_4$, wherein $Z^A$ is —CH$_2$—, and $R_4$ is an optionally substituted bicyclic cycloalkyl or an optionally substituted bicyclic cycloalkenyl. For example, $R_1$ is —$Z^A R_4$, wherein $Z^A$ is —CH$_2$—, and $R_4$ is an optionally substituted 5-10 membered bicyclic cycloalkyl. In other examples, $R_1$ is $Z^A R_4$, wherein $Z^A$ is —CH$_2$—, and $R_4$ is bicyclo[1.1.1]pentane-yl, bicyclo[2.1.1]hexane-yl, bicyclo[2.2.1]heptane-yl, bicyclo[2.2.2]octane-yl, bicyclo[3.1.1]heptane-yl, bicyclo[3.2.1]octane-yl, or bicyclo[3.3.2]decane-yl, each of which is optionally substituted. In several examples, $R_1$ is —$Z^A R_4$, wherein $Z^A$ is —CH$_2$—, and $R_4$ is bicyclo[1.1.1]pentane-yl, bicyclo[2.1.1]hexane-yl, bicyclo[2.2.1]heptane-yl, bicyclo[2.2.2]octane-yl, bicyclo[3.1.1]heptane-yl, bicyclo[3.2.1]octane-yl, or bicyclo[3.3.2]decane-yl, each of which is unsubstituted. In other examples, $R_1$ is —$Z^A R_4$, wherein $Z^A$ is —CH$_2$—, and $R_4$ is an optionally substituted 7-10 membered bicyclic cycloalkenyl. For instance, $R_1$ is —$Z^A R_4$, wherein $Z^A$ is —CH$_2$—, and $R_4$ is bicyclo[2.2.1]hept-en-yl, bicyclo[2.2.2]oct-en-yl, bicyclo[3.2.1]oct-en-yl, or bicyclo[3.3.2]dec-en-yl, each of which is optionally substituted. In other instances, $R_1$ is —$Z^A R_4$, wherein $Z^A$ is —CH$_2$—, and $R_4$ is bicyclo[2.2.1]hept-en-yl, bicyclo[2.2.2]oct-en-yl, bicyclo[3.2.1]oct-en-yl, or bicyclo[3.3.2]dec-en-yl, each of which is unsubstituted.

In other embodiments, $R_1$ is —$Z^A R_4$, wherein $Z^A$ is a bond, and $R_4$ is an optionally substituted cycloaliphatic or an optionally substituted heterocycloaliphatic. For example, $R_1$ is —$Z^A R_4$, wherein $Z^A$ is a bond, and $R_4$ is an optionally substituted monocyclic cycloaliphatic or an optionally substituted bicyclic cycloaliphatic. In several examples, $R_1$ is —$Z^A R_4$, wherein $Z^A$ is a bond, and $R_4$ is an optionally substituted 3-7 membered monocyclic cycloalkyl or cycloalkenyl, either of which is optionally substituted. For instance, $R_1$ is —$Z^A R_4$, wherein $Z^A$ is a bond, and $R_4$ is an optionally substituted 3-7 membered optionally substituted monocyclic cycloalkyl. In other examples, $R_1$ is —$Z^A R_4$, wherein $Z^A$ is a bond, and $R_4$ is cyclopropyl, cyclobutyl, cyclopentyl, cyclohexyl, or cycloheptyl, each of which is optionally substituted. In alternative examples, $R_1$ is —$Z^A R_4$, wherein $Z^A$ is a bond, and $R_4$ is an unsubstituted cyclopropyl, cyclobutyl, cyclopentyl, cyclohexyl, or cycloheptyl.

In other embodiments, $R_1$ is —$Z^A R_4$, wherein $Z^A$ is a bond, and $R_4$ is an optionally substituted bicyclic cycloaliphatic. For example, $R_1$ is —$Z^A R_4$, wherein $Z^A$ is a bond, and $R_4$ is an optionally substituted bicyclic cycloalkyl or an optionally substituted bicyclic cycloalkenyl. For example, $R_1$ is —$Z^A R_4$, wherein $Z^A$ is a bond, and $R_4$ is an optionally substituted 5-10 membered bicyclic cycloalkyl. In other examples, $R_1$ is —$Z^A R_4$, wherein $Z^A$ is a bond, and $R_4$ is bicyclo[1.1.1]pentane-yl, bicyclo[2.1.1]hexane-yl, bicyclo[2.2.1]heptane-yl, bicyclo[2.2.2]octane-yl, bicyclo[3.1.1]heptane-yl, bicyclo[3.2.1]octane-yl, or bicyclo[3.3.2]decane-yl, each of which is optionally substituted. In several examples, $R_1$ is —$Z^A R_4$, wherein $Z^A$ is a bond, and $R_4$ is bicyclo[1.1.1]pentane-yl, bicyclo[2.1.1]hexane-yl, bicyclo[2.2.1]heptane-yl, bicyclo[2.2.2]octane-yl, bicyclo[3.1.1]heptane-yl, bicyclo[3.2.1]octane-yl, or bicyclo[3.3.2]decane-yl, each of which is unsubstituted. In other examples, $R_1$ is —$Z^A R_4$, wherein $Z^A$ is a bond, and $R_4$ is an optionally substituted 7-10 membered bicyclic cycloalkenyl. For instance, $R_1$ is —$Z^A R_4$, wherein $Z^A$ is a bond, and $R_4$ is bicyclo[2.2.1]hept-en-yl, bicyclo[2.2.2]oct-en-yl, bicyclo[3.2.1]oct-en-yl, or bicyclo[3.3.2]dec-en-yl, each of which is optionally substituted. In other instances, $R_1$ is —$Z^A R_4$, wherein $Z^A$ is a bond, and $R_4$ is bicyclo[2.2.1]hept-en-yl, bicyclo[2.2.2]oct-en-yl, bicyclo[3.2.1]oct-en-yl, or bicyclo[3.3.2]dec-en-yl, each of which is unsubstituted.

In other embodiments, $R_1$ is —$Z^A R_4$, wherein $Z^A$ is —CH$_2$—, and $R_4$ is an optionally substituted heterocycloaliphatic. In several examples, $R_1$ is —$Z^A R_4$, wherein $Z^A$ is —CH$_2$—, and $R_4$ is an optionally substituted monocyclic or bicyclic heterocycloaliphatic. In other examples, $R_1$ is —$Z^A R_4$, wherein $Z^A$ is —CH$_2$—, and $R_4$ is an optionally substituted 5-10 membered optionally substituted monocyclic or bicyclic heterocycloaliphatic having 1-3 heteroatoms independently selected from N, O, and S. In other examples, $R_1$ is —$Z^A R_4$, wherein $Z^A$ is —CH$_2$—, and $R_4$ is an optionally substituted monocyclic 5-8 membered heterocycloaliphatic having 1-3 heteroatoms independently selected from N, O, and S. In other examples, $R_1$ is —$Z^A R_4$, wherein $Z^A$ is —CH$_2$—, and $R_4$ is piperidine-yl, piperazine-yl, morpholine-yl, pyrrolidine-yl, 3-pyrroline-yl, azepane-yl, pyrazolidine-yl, or pyran-yl, each of which is optionally substituted with 1-3 of halo, —OH, —CN, $C_{1-6}$ straight or branched aliphatic, (alkoxy)carbonyl, alkylamino, combinations thereof, or the like.

In other embodiments, $R_1$ is —$Z^A R_4$, wherein $Z^A$ is a bond, and $R_4$ is an optionally substituted heterocycloaliphatic. In several examples, $R_1$ is —$Z^A R_4$, wherein $Z^A$ is a bond, and $R_4$ is an optionally substituted monocyclic or bicyclic heterocycloaliphatic. In other examples, $R_1$ is —$Z^AR_4$, wherein $Z^A$ is a bond, and $R_4$ is an optionally substituted 5-10 membered optionally substituted monocyclic or bicyclic heterocycloaliphatic having 1-3 heteroatoms independently selected from N, O, and S. In other examples, $R_1$ is —$Z^AR_4$, wherein $Z^A$ is a bond, and $R_4$ is an optionally substituted monocyclic 5-8 membered heterocycloaliphatic having 1-3 heteroatoms selected from N, O, and S. In other examples, $R_1$ is —$Z^AR_4$, wherein $Z^A$ is a bond, and $R_4$ is piperidine-yl, piperazine-yl, morpholine-yl, pyrrolidine-yl, 3-pyrroline-yl, azepane-yl, pyrazolidine-yl, or pyran-yl, each of which is optionally substituted with 1-3 of halo, —OH, —CN, $C_{1-6}$ straight or branched aliphatic, (alkoxy)carbonyl, alkylamino, or combinations thereof.

In several embodiments, $R_1$ is one selected from:

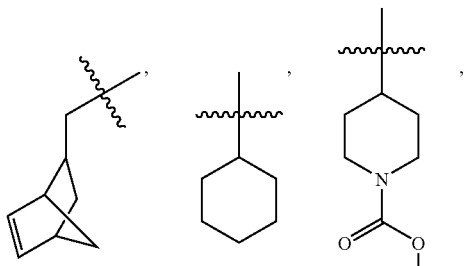

In several embodiments, $R_1$ is one selected from:

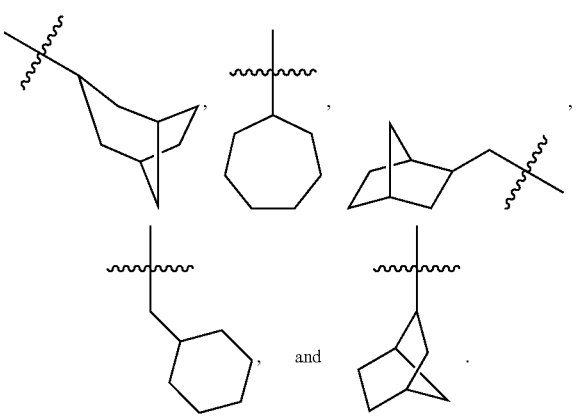

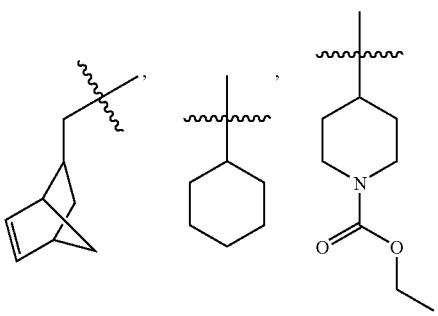

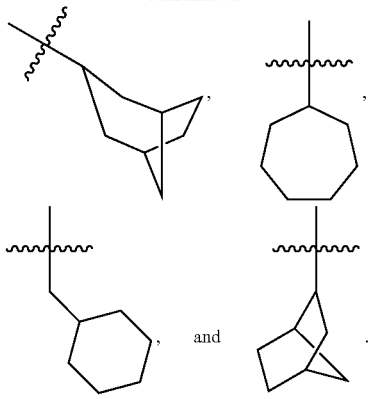

2. Substituent $R_2$ and q-Term $R_2$ is —$Z^BR_5$, wherein each $Z^B$ is independently a bond or an optionally substituted branched or straight $C_{1-12}$ aliphatic chain wherein up to two carbon units of $Z^B$ are optionally and independently replaced by —CO—, —CS—, —$CONR^B$—, —$CONR^BNR^B$—, —$CO_2$—, —OCO—, —$NR^BCO_2$—, —O—, —$NR^BCONR^B$—, —$OCONR^B$—, —$NR^BNR^B$—, —$NR^BCO$—, —S—, —S(O)—, —$S(O)_2$—, —$NR^B$—, —$S(O)_2NR^B$—, —$NR^BS(O)_2$—, or —$NR^BS(O)_2NR^B$—. Each $R_5$ is independently $R^B$, halo, —OH, —CN, or —$OCF_3$. Each $R^B$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In several embodiments, $R_2$ is hydrogen. For example, in some embodiments, q is 0 or each $R_2$ is hydrogen.

In several embodiments, when q is 1, 2, or 3, $R_2$ is attached to the core structure of formula I at the 6 position, 7 position, 8 position, or combinations thereof. For example, $R_2$ is attached at the 6 or 7 position, or a combination thereof.

In several embodiments, $R_2$ is an optionally substituted amino. For example, $R_2$ is an (aliphatic)amino, (cycloaliphatic)amino, or combinations thereof, each of which is optionally substituted.

In several embodiments, $R_2$ is an optionally substituted amido. For example, $R_2$ is an (alkyl(carbony))lamino, (cycloalkyl(carbonyl))amino, (alkyl(amino))carbonyl, (cycloalkyl(amino))carbonyl, or combination thereof, each of which is optionally substituted.

In several embodiments, $R_2$ is an optionally substituted (alkyl(amino))carbonyl, an optionally substituted (aliphatic)carbonyl, or an optionally substituted (alkoxy)carbonyl. For example, $R_2$ is a (methyl(amino))carbonyl, (ethyl(amino))carbonyl, (propyl(amino))carbonyl, or combinations thereof, each of which is optionally substituted. In other examples, $R_2$ is a (methoxy)carbonyl, (ethoxy)carbonyl, (propoxy)carbonyl, (butoxy)carbonyl, or combinations thereof, each of which is optionally substituted. Additional examples of $R_2$ includes (methyl)carbonyl, (ethyl)carbonyl, (propyl)carbonyl, (butyl)carbonyl, or combinations thereof, each of which is optionally substituted.

In several embodiments, q is 1 or 2, and each $R_2$ is independently halo, or methoxy.

In several embodiments, —$R_2$ is halo, hydrogen, or methoxy. Other embodiments include 2 $R_2$ groups (i.e., q=2), wherein each is methoxy.

3. Groups $Z_1$-$Z_4$

Each of $Z_1$-$Z_4$ is independently a bond or —$CR_3R'_3$—, —$NR_3$—, or —O— wherein each $R_3$ and $R'_3$ is —$Z^CR_6$, wherein each $Z^C$ is independently a bond or an optionally substituted branched or straight $C_{1-12}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —(O)—, —S(O)$_2$—, —NR$^C$—, —S(O)$_2$NR$^C$—, —NR$^C$S(O)$_2$—, or —NR$^C$S(O)$_2$NR$^C$—. Each $R_6$ is independently $R^C$, halo, —OH, —CN, or —OCF$_3$. Each $R^C$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

Alternatively, $R_3$ and $R'_3$ together form an oxo group.

In one embodiment, one of $Z_1$, $Z_2$, $Z_3$, or $Z_4$ is a bond, one of $Z_1$, $Z_2$, $Z_3$, or $Z_4$ is —NR$_3$— or —O—, and the remaining $Z_1$, $Z_2$, $Z_3$, or $Z_4$ are —CR$_3$R'$_3$—, wherein each $R_3$ and $R'_3$ is —$Z^C$R$_6$, wherein each $Z^C$ is independently a bond or an optionally substituted branched or straight $C_{1-12}$ aliphatic chain wherein up to two carbon units of $Z^C$ are optionally and independently replaced by —CO—, —CS—, —CONR$^C$—, —CONR$^C$NR$^C$—, —CO$_2$—, —OCO—, —NR$^C$CO$_2$—, —O—, —NR$^C$CONR$^C$—, —OCONR$^C$—, —NR$^C$NR$^C$—, —NR$^C$CO—, —S—, —S(O)—, —S(O)$_2$—, —NR$^C$—, —S(O)$_2$NR$^C$—, —NR$^C$S(O)$_2$—, or —NR$^C$S(O)$_2$NR$^C$—; each $R_6$ is independently $R^C$, halo, —OH, —CN, or —OCF$_3$; each $R^C$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl; or $R_3$ and $R'_3$ together form an oxo group.

In another embodiment, $Z_1$, $Z_2$, $Z_3$, and $Z_4$ together form:

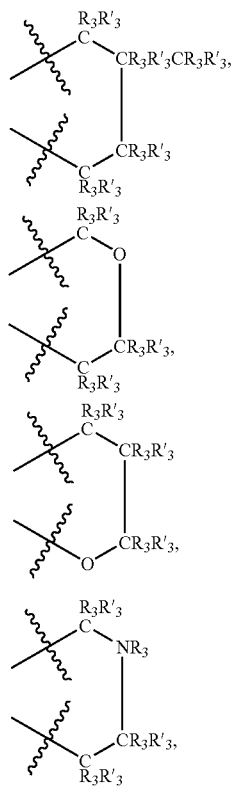

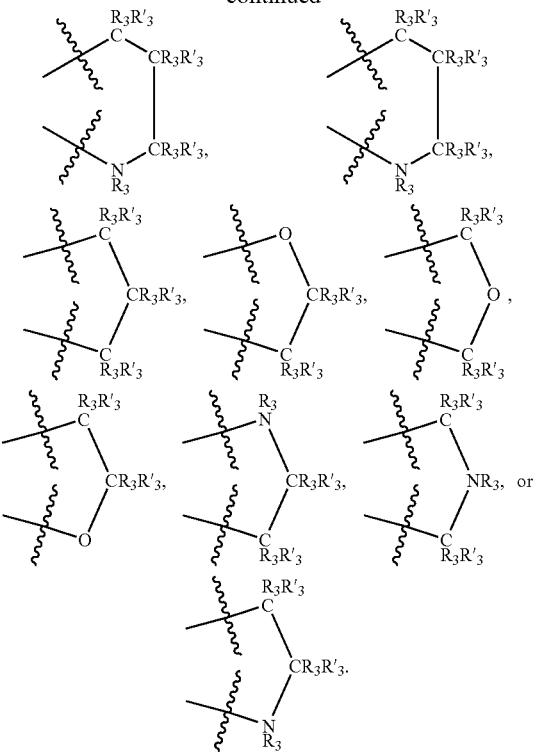

In one embodiment, $Z_1$, $Z_2$, $Z_3$, and $Z_4$ together form

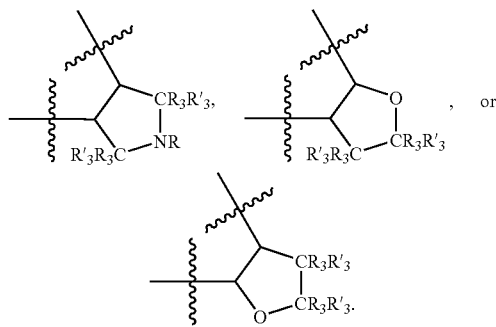

In another embodiment, $Z_1$, $Z_2$, $Z_3$, and $Z_4$ together form

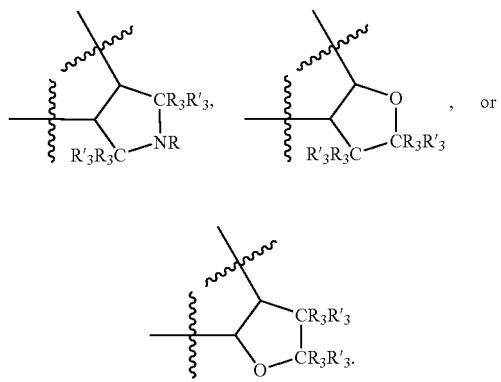

In an alternative embodiment, $Z_1$, $Z_2$, $Z_3$, and $Z_4$ together form
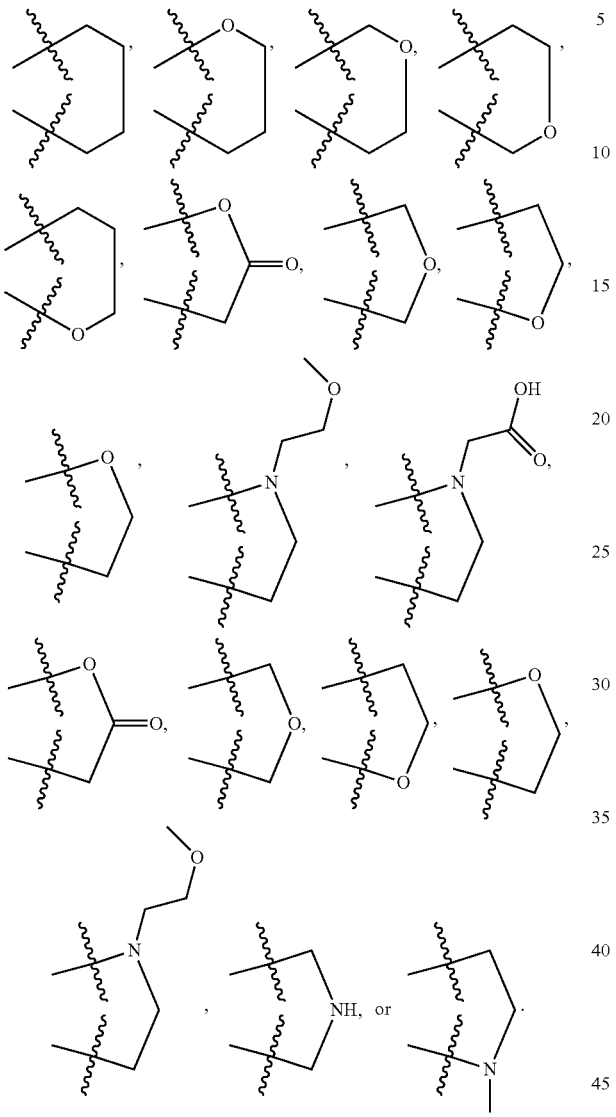
In one embodiment, $Z_1$, $Z_2$, $Z_3$, and $Z_4$ together form
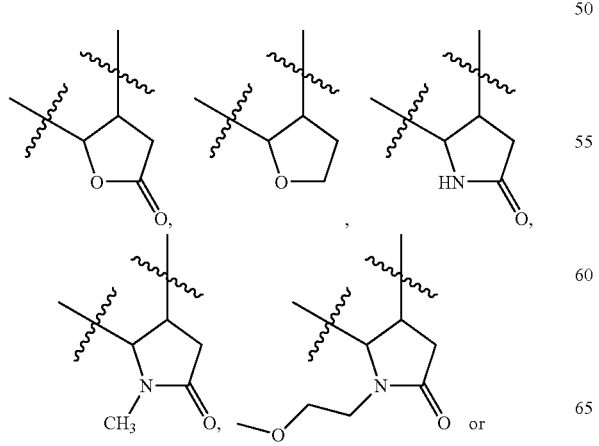
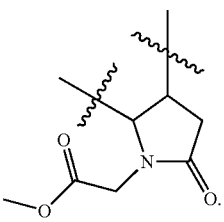
In another embodiment, $Z_1$, $Z_2$, $Z_3$, and $Z_4$ together form
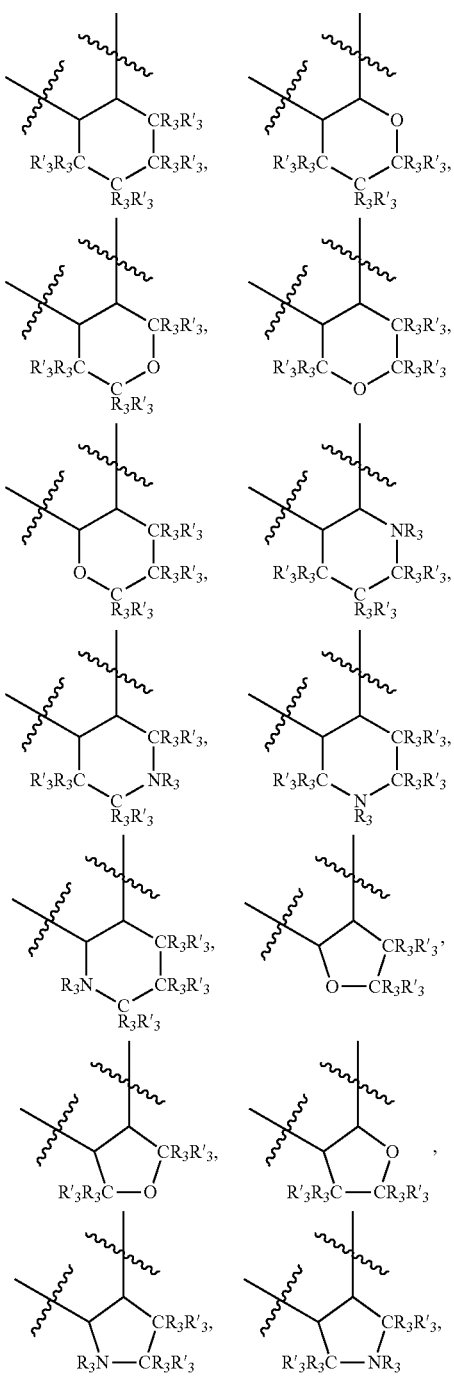

-continued

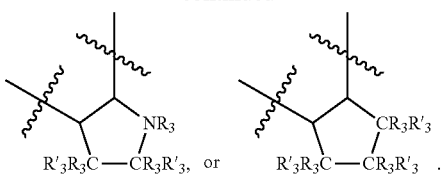

Variables n, m, p, and q:

p is 0-3, m is 0-3, and p+m is 3 or 4.

n is 0 or 1.

q is 0-4.

In several embodiments, m and p are both 2.

In several embodiments, m and p are each 0, 1, or 2. In other embodiments, n is 0 or 1. In several embodiments, q is 0, 1, 2, 3, or 4.

In one example, p is 2 and m is 2. In another example, p is 2, m is 2, n is 1, and q is 0.

B. Sub-Generic Compounds

Another aspect of the present invention provides compounds of formula Ia:

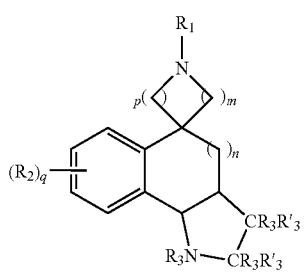

Ia or a pharmaceutically acceptable salt thereof, wherein $R_1$, $R_2$, $R_3$, $R'_3$, m, n, p, and q are defined above in formula I.

Another aspect of the present invention provides compounds of formula Ib:

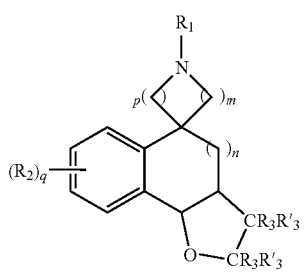

Ib or a pharmaceutically acceptable salt thereof, wherein $R_1$, $R_2$, $R_3$, $R'_3$, m, n, p, and q are defined above in formula I.

C. Exemplary Compounds

Exemplary compounds of the present invention include, but are not limited to, those illustrated in Table 1, below.

TABLE 1

Exemplary compounds of formulae I, Ia, and Ib.

TABLE 1-continued
Exemplary compounds of formulae I, Ia, and Ib.
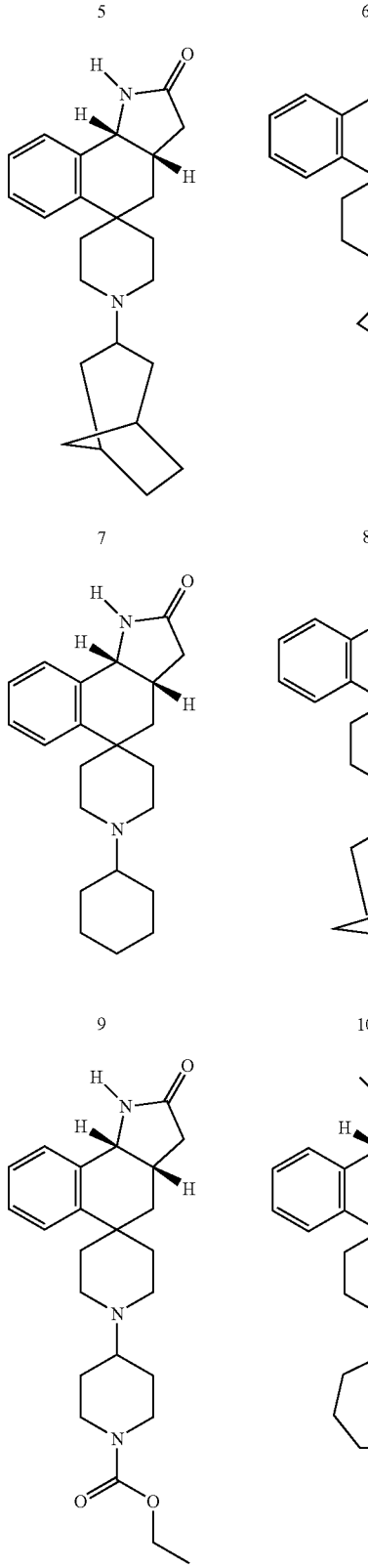
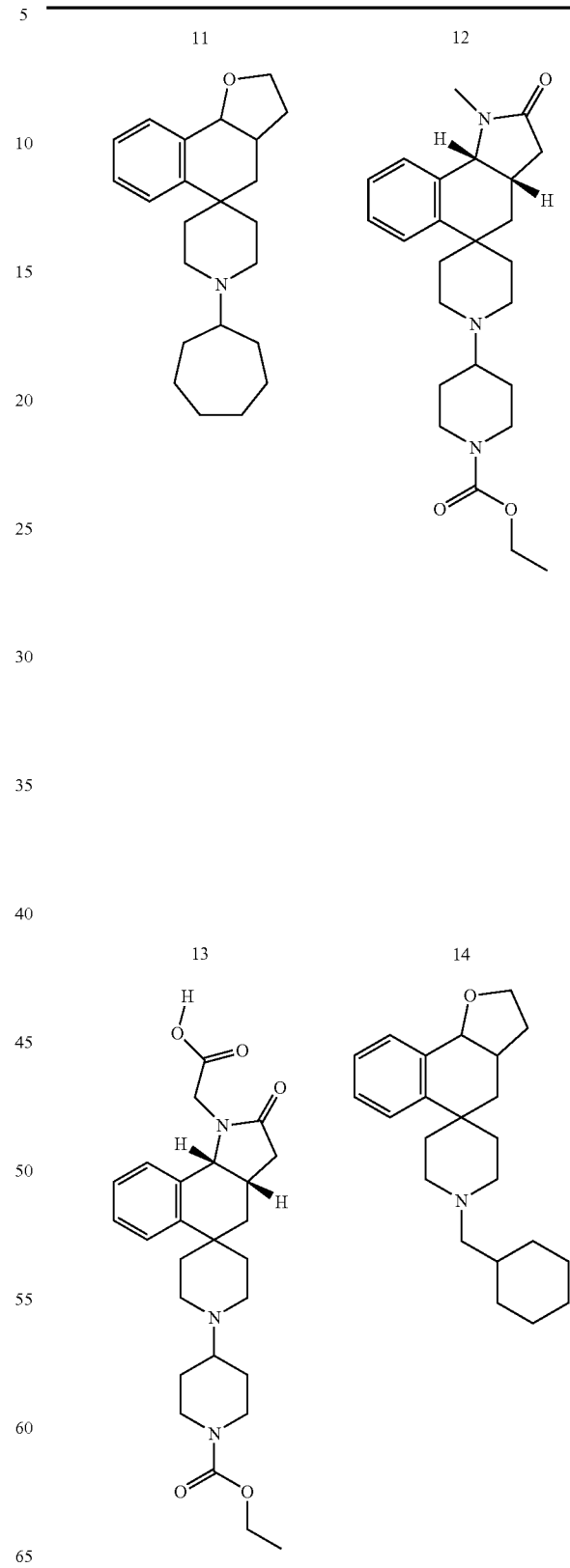

TABLE 1-continued
Exemplary compounds of formulae I, Ia, and Ib.
| 15 | 16 |
|---|---|
| 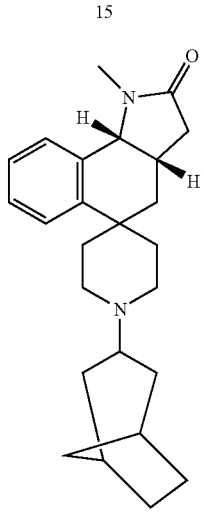 | 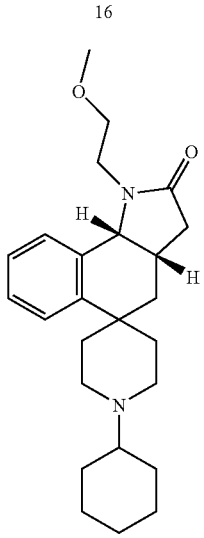 |
| 17 | 18 |
|---|---|
| 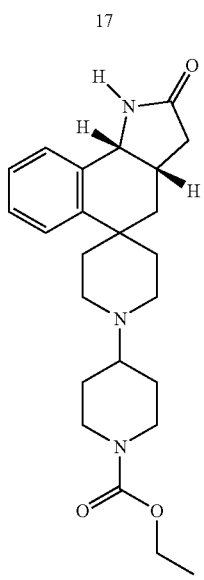 | 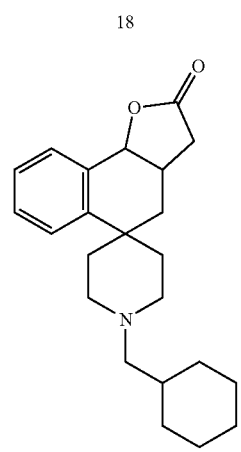 |
TABLE 1-continued
Exemplary compounds of formulae I, Ia, and Ib.
| 19 | 20 |
|---|---|
| 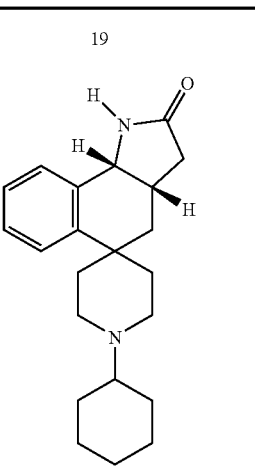 | 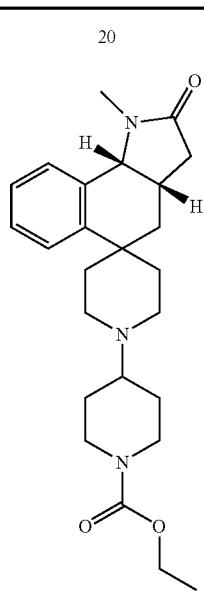 |
| 21 | 22 |
|---|---|
| 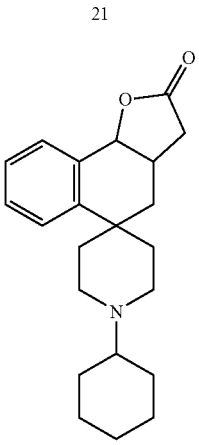 | 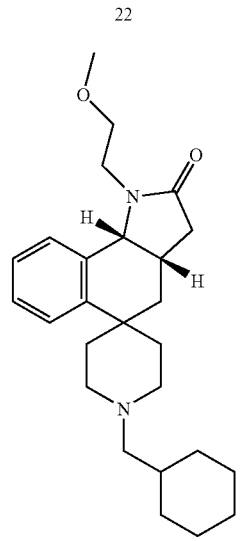 |

TABLE 1-continued

Exemplary compounds of formulae I, Ia, and Ib.

23

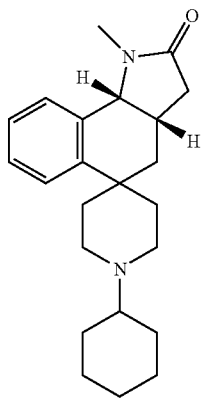

24

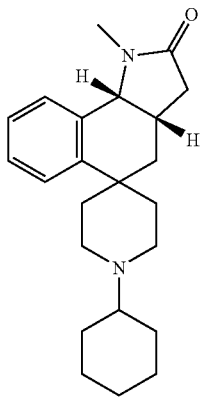

29

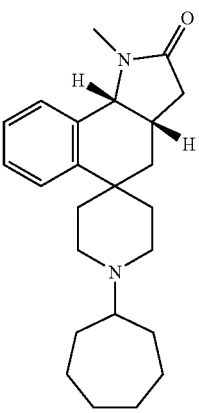

30

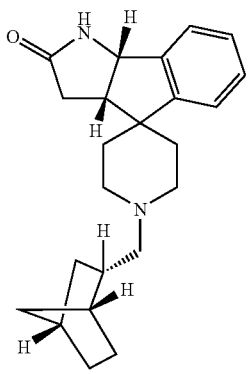

25

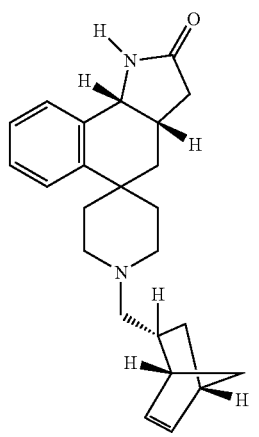

26

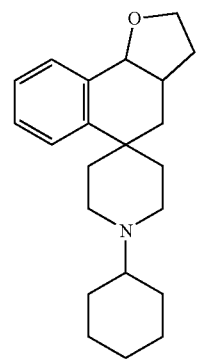

31

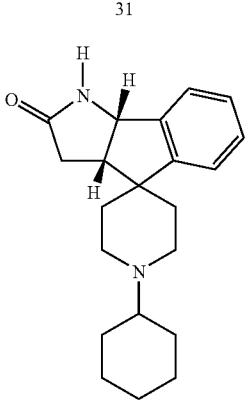

32

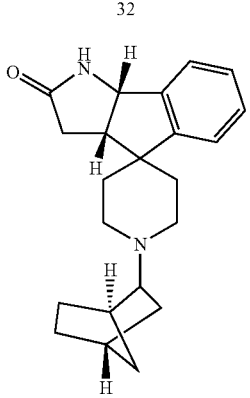

27

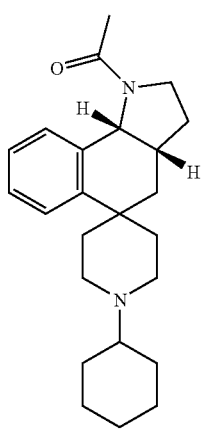

28

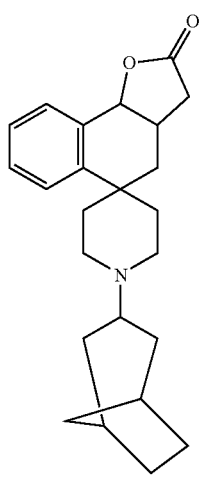

III. Preparation of Compounds

The compounds of formulae (I, Ia, and Ib) may be synthesized from commercially available or known starting materials by known methods. Exemplary synthetic routes to produce compounds of formulae (I, Ia, and Ib) are provided below in the schemes below.

For the purpose of clarity in these schemes, $Z_4$ is a bond and $Z_3$ is —$CH_2$—. The schemes are intended, however, as illustrative and are not limitative. Methods described are applicable to other variants of $Z_4$ and $Z_3$.

In one method, compounds of the invention wherein $Z_1$ is $NR_3$ and $Z_2$ is C(O), may be prepared as illustrated in Scheme 1.

Scheme 1
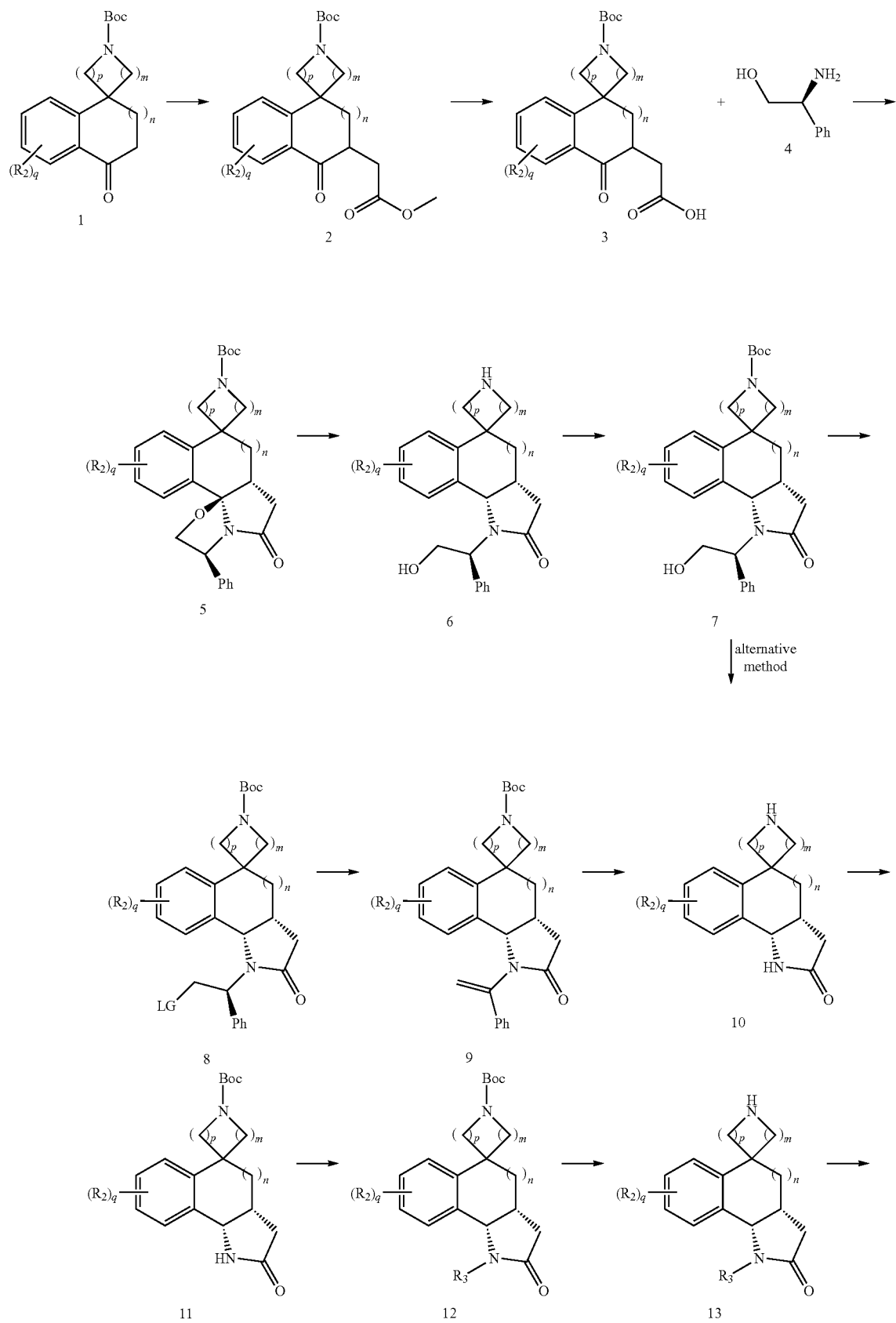

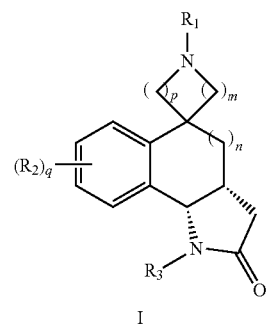

Referring to Scheme 1, the benzocycloalkanone 1 is alkylated with, for example, methylbromoacetate in the presence of a strong base such as, for example, lithium bis(timethylsilyl)amide to provide the intermediate ester 2. Hydrolysis of the ester using known conditions provides the acid 3 which reacts with the phenylglycinol 4 to provide the intermediate 5. reductive ring opening of 5 with triethylsilane in the presence of titanium tetrachloride provides the glycinol 6. Reprotection of 6 provides the Boc derivative 7 which is converted to the intermediate 8. In some methods, wherein LG in 8 is a pyridinium salt, 8 is prepared by treatment of 7 with triflic anhydride in the presence of pyridine. In other methods, wherein LG in 8 is Cl, 8 is prepared by treatment of 7 with methanesulfonyl chloride in the presence of triethyl amine. Treatment of 8 with a strong base such as, for example, potassium t-butoxide provides the enamine 9. Hydrolysis of 9 with hydrochloric acid leads to the deprotected lactam 10. In an alternative method, 10 is obtained directly from 7 by treatment of 7 with lithium hydroxide in dimethyl sulfoxide at elevated temperatures. Reprotection of 10 to provide the Boc derivative 11 followed by alkylation of the lactam nitrogen of 11 by treatment of 11 with sodium hydride and an aliphatic halide provides intermediates 12. Deprotection of 12 provides the amine 13. Reductive amination of 13 by treatment of 13 with a ketone in the presence of sodium triacetoxyborohydride in the presence of a Lewis acid such as, for example, titanium isopropoxide provides compounds of the invention I.

In some embodiments, compounds of the invention wherein $Z_2$ is —CH$_2$— and $Z_1$ is NR$_3$, may be prepared as illustrated in Scheme 2.

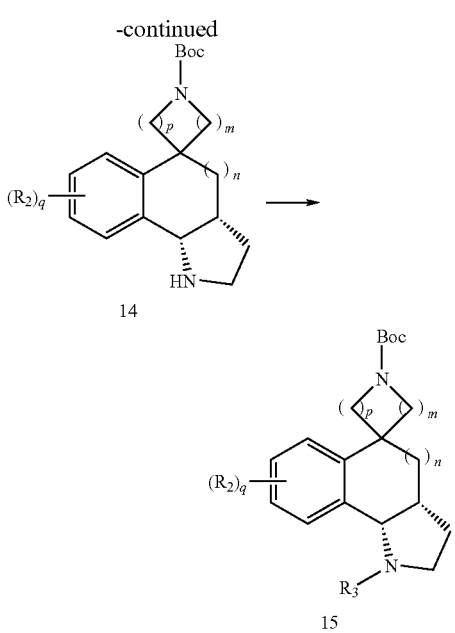

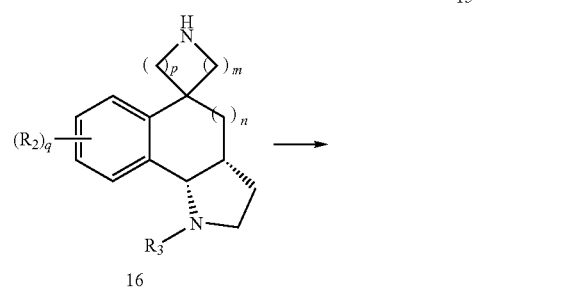

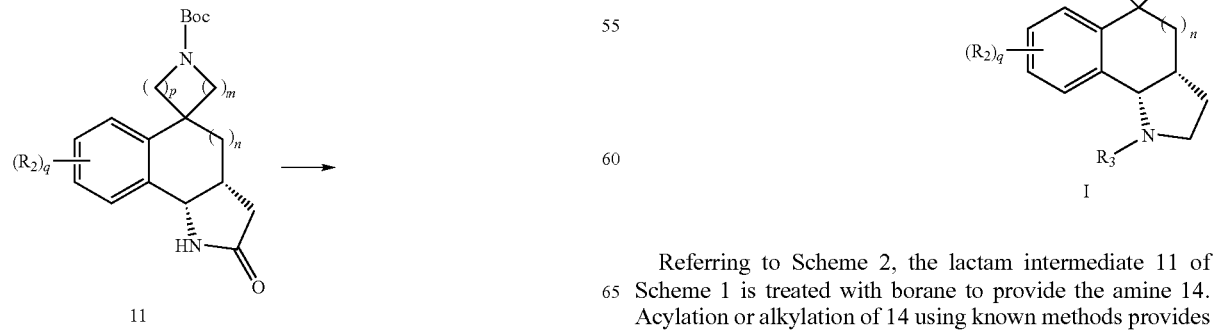

Referring to Scheme 2, the lactam intermediate 11 of Scheme 1 is treated with borane to provide the amine 14. Acylation or alkylation of 14 using known methods provides the substituted amine 16 wherein R$_3$ is acyl or aliphatic.

Reductive amination of 16 with a ketone as previously described provides certain embodiments of the invention I.

In other embodiments, antipodes of the intermediates and compounds of the invention in Schemes 1 and 2 may be prepared using the antipode of phenylglycinol 4.

In certain embodiments, wherein $Z_1$ is —O— and $Z_2$ is —C(O)—, compounds of the invention may be prepared as illustrated in Scheme 3.

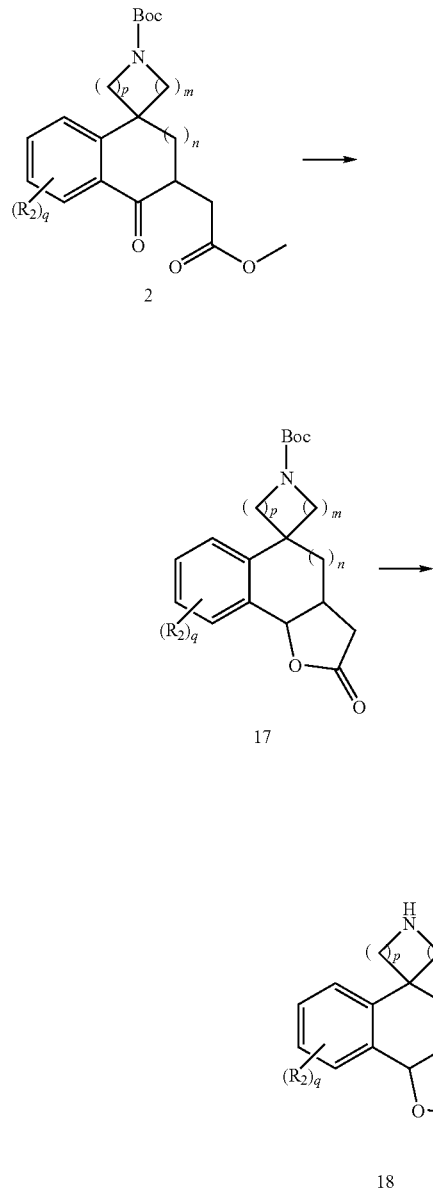

Referring to Scheme 2, the intermediate keto-ester 2 is treated with zinc borohydride to provide the lactone 16 wherein the lactone ring has the trans configuration. Removal of the Boc group of 17 provides the amino-lactone 18 which is converted to compounds of the invention I by reductive amination as previously described.

In yet another method, compounds of the invention wherein $Z_1$ is —O— and $Z_2$ is —CH$_2$— may be prepared as illustrated in Scheme 4.

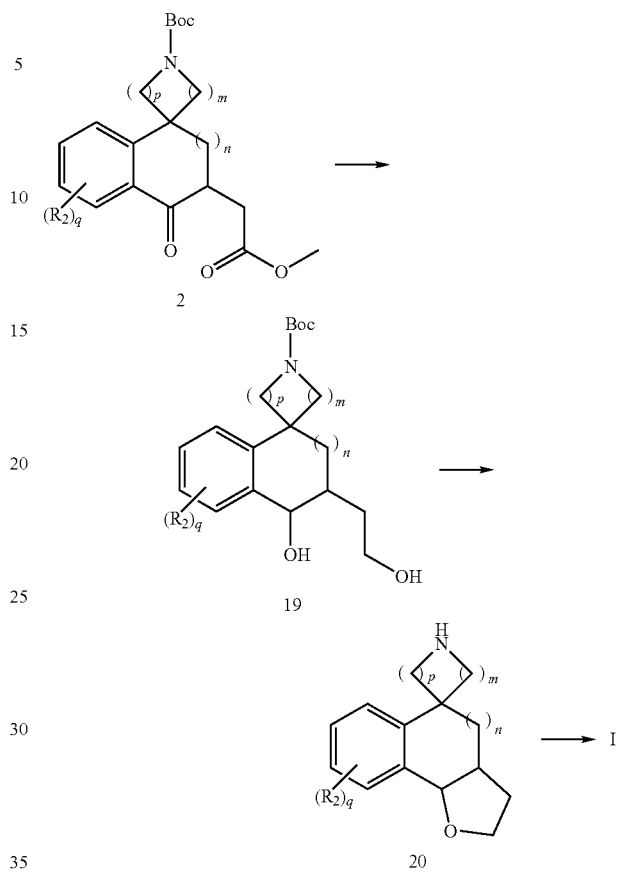

Referring to Scheme 4, treatment of the keto-ester 2 with lithium borohydride results in providing the diol 19. Reaction of 19 with boron trifluoride etherate leads to ring closure and concomitant removal of the Boc group to provide the amine-furan 20 wherein the furan ring is cis-fused. Reductive amination of 20 as previously described provides compounds of the invention I.

Iv. Formulations, Administrations, and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, Ia, and Ib) are selective modulators of $M_1$, $M_2$ and $M_4$. More preferably, the compounds of formulae (I, Ia, and Ib) are selective modulators of $M_1$ and/or $M_4$. Yet more preferably, certain compounds of formulae (I, Ia, and Ib) are selective modulators of $M_1$. Or, preferably, certain compounds of formulae (I, Ia, and Ib) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae (I, Ia, and Ib), or an embodiment thereof as set forth herein.

According to another embodiment, the present invention provides a method of treating a disease mediated by a muscarinic receptor including the step of administering to said mammal a composition comprising a compound of formulae (I, Ia, and Ib), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, or GI disturbances.

According to a preferred embodiment, the present invention is useful for treating or reducing the severity of psychosis, Alzheimer's disease, pain, or Parkinson's disease. All references cited within this document are incorporated herein by reference.

V. Preparations and Examples

In order that the invention described therein may be more fully understood, the following examples are set forth. It should be understood that these examples are for illustrative purposes only and are not to be construed as limiting this invention in any manner.

$^1$H-NMR spectra were recorded at 300 MHz using a Bruker AMX 300 instrument. Mass spectroscopy samples were analyzed on a MicroMass ZQ or Quattro II mass spectrometer operated in single MS mode with electrospray ionization. Samples were introduced into the mass spectrometer using chromatography, using Zorbax SB C18 column, 3.0×150 mm. Flow rate: 1.0 mL/minute. Detection: 254 & 214 nm. Mobile phase for all mass spectroscopy analysis consisted of acetonitrile-water mixtures with 0.2% formic acid as a modifier using 10-90% acetonitrile and water gradient. As used herein, the term "$R_t$" refers to the HPLC retention time, in minutes, associated with the compound. HPLC purification refers to C-18 reverse phase using Gilson instrument, YMC combiprep ProC18 column, 20×100 mm. Flow rate is 20 ml/minute. Mobile phase consisted of water with 0.1% TFA and acetonitrile with 0.1% TFA. Running time is 10 minutes.

Preparation A: Synthesis of tert-butyl 4-oxo-3,4-dihydro-2H-spiro[naphthalene-1,4'-piperidine]-1'-carboxylate

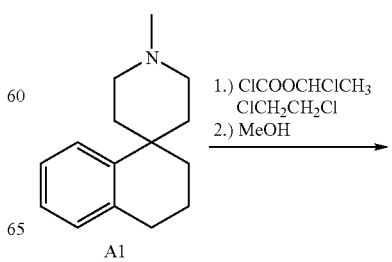

A1

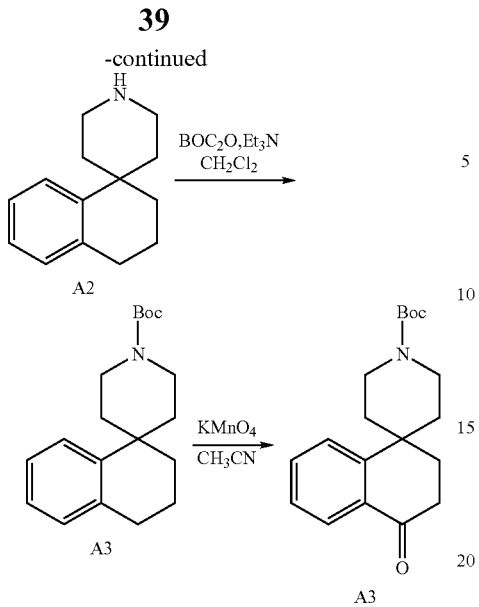

1'-Methyl-3,4-dihydro-2H-spiro[naphthalene-1,4'-piperidine] (A1) was prepared from commercially available 4-(3-phenylpropyl)pyridine as previously described. (Eberehard Reimann, Johann Speckbacher, Hermann Lotter, Arch Pharm. (Weinheim), 320 (1987), 385-393. Graham L. Patrick, J. Chem. Soc. Perkin Trans 1, (1995) 1273-1279).

To a solution of the N-methylpiperidine (A1) (37 g, 172 mmol) in 1,2-dichloroethane (250 ml) was added 1-chloroethyl chloroformate (20.7 ml, 190 mmol) at 0° C. The solution turned to a solid. After 0.5 hours at room temperature, the reaction mixture was heated under reflux for 15 hours. After concentration, the residue was dissolved in methanol (250 ml) and heated at 50° C. for 2 hours. The mixture was cooled to room temperature, the precipitate was filtered and washed with ether to produce 3,4-dihydro-2H-spiro[naphthalene-1,4'-piperidine] HCl salt (A2). The filtrate was concentrated, suspended in ether, filtered, and the solid washed with MeOH and ether to give additional 3,4-dihydro-2H-spiro[naphthalene-1,4'-piperidine] HCl salt (A2). LC-MS: m/e=202.1 (M+H). $R_f$=1.61 min. $^1$H-NMR (500 MHz, CDCl$_3$): 9.74 (s, 2H), 7.58 (d, J=7.9, 1H), 7.22 (t, J=7.8, 1H), 7.14 (t, J=7.9, 1H), 7.08 (d, J=8.0, 1H), 3.47 (d, J=12.4, 2H), 3.22-3.18 (m, 2H), 2.88 (t, J=4.9, 2H), 2.81 (t, J=6.2, H), 2.60 (td, 2H), 1.93-1.89 (m, 2H), 1.83-1.77 (m, 2H).

A solution of the piperidine salt (A2) (2.2 g, 9.2 mmol) in dichloromethane (100 ml) was treated with Et$_3$N (4 ml, 28.9 mmol) and di-tert-butyldicarbonate (2.5 g, 11.4 mmol) at room temperature for 2 hours. The reaction mixture was washed with dilute aqueous HCl, and the organic phase was washed with aqueous sodium bicarbonate, dried (Na$_2$SO$_4$), and concentrated to give tert-butyl 3,4-dihydro-2H-spiro[naphthalene-1,4'-piperidine]-1'-carboxylate (A3) as a white solid. LC-MS: m/e=246.0 (M+H–tBu). $R_f$=4.16 min. $^1$H-NMR (500 MHz, CDCl$_3$): 7.27 (d, J=7.9, 1H), 7.10 (td, J=7.4, 1.6, 1H), 7.05 (td, J=7.3, 1.3, 1H), 7.00 (d, J=7.6, 1H), 3.93 (br.d, J=13.3, 2H), 2.92 (td, J=13.2, 2.8, 2H), 2.71 (t, J=6.3, H), 1.90 (td, J=13.4, 5.0, 2H), 1.82-1.80 (m, 2H), 1.72-1.67 (m, 2H), 1.49-1.46 (m, 2H), 1.42 (s, 9H).

To a solution of the Boc-piperidine (602 mg, 2 mmol) in acetonitrile (10 ml) was added potassium permanganate (KMnO$_4$, 950 mg, 6 mmol). The reaction mixture was stirred at 70° C. for 15 hours, filtered through Celite, and the filter cake was washed with dichloromethane. The filtrate and washings were concentrated and the residue was dissolved in acetonitrile (10 ml) and reacted with KMnO$_4$ (950 mg, 6 mmol) at 70° C. for another 24 hours. After filtration, washing and concentrating, the residue was purified by flash column chromatography (CH$_2$Cl$_2$/CH$_3$CN: 1:0 to 9:1) to provide tert-butyl 4-oxo-3,4-dihydro-2H-spiro[naphthalene-1,4'-piperidine]-1'-carboxylate (A4). LC-MS: m/e=260.0 (M+H–tBu). $R_f$=3.46 min. $^1$H-NMR (500 MHz, CDCl$_3$): 8.07 (dd, J=1.5, 7.8, 1H), 7.60-7.57 (td, J=7.9, 1.2, 1H), 7.50 (d, J=7.9, 1H), 7.36 (t, J=7.6, 1.0, 1H), 4.10 (br.d, J=13.2, 2H), 3.08 (t, J=13.8, 2H), 2.71 (t, J=6.7, 2H), 2.27 (t, J=6.9, 2H), 2.05 (td, J=13.4, 4.7, 2H), 1.73 (br.d, J=13.2, 2H), 1.52 (s, 9H).

Preparation 1: (3aR,9bS)-1,3a,4,9b-tetrahydrospiro[benzo[g]indole-5,4'-piperidin]-2(3H)-one

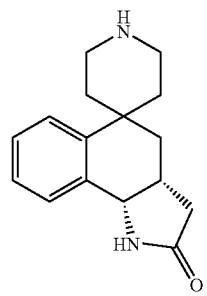

Step 1: tert-butyl 3-(2-methoxy-2-oxoethyl)-4-oxo-3,4-dihydro-2H-spiro[naphthalene-1,4'-piperidine]-1'-carboxylate

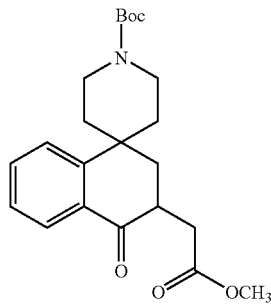

At –78° C., lithium bis(trimethylsilyl)amide (Aldrich, 1.0M in THF, 10 ml, 10 mmol) was added to a solution of tert-butyl 3-(2-methoxy-2-oxoethyl)-4-oxo-3,4-dihydro-2H-spiro[naphthalene-1,4'-piperidine]-1'-carboxylate (2.0 g, 6.35 mmol) in dry THF (40 ml) under nitrogen. After 1 h at –78° C., methyl bromoacetate (1 ml, 10.8 mmol) was added and the cooling bath was removed and the reaction mixture was kept at r.t. for 15 h. The analytical HPLC spectrum of the reaction mixture indicated that there was still some starting material. After concentration, the residue was dissolved in EtOAc and washed with brine. The aqueous phase was re-extracted. The combined organic phases were dried (Na$_2$SO$_4$), filtered and evaporated to give the crude tert-butyl 3-(2-methoxy-2-oxoethyl)-4-oxo-3,4-dihydro-2H-spiro[naphthalene-1,4'-piperidine]-1'-carboxylate (3.0 g) which contains some starting material. LC-MS: m/e=332.1 (M+H−C(CH3)3), 300.1 (M+H−Me−OC(CH3)3, 100%). Rt=3.53 min.

Step 2: 2-(1'-(tert-butoxycarbonyl)-4-oxo-3,4-dihydro-2H-spiro[naphthalene-1,4'-piperidine]-3-yl)acetic acid

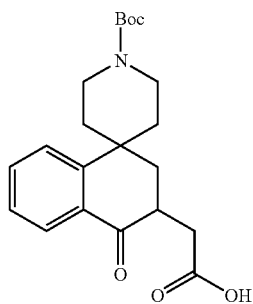

A solution of the crude methyl ester of Step 1 (3.0 g) in methanol (50 ml) and 20% aqueous KOH (5 ml) was heated under reflux for 1 h. Evaporation and the residue was dissolved in water, extracted with EtOAc. The organic phase was washed with 1N NaOH (several times), and the combined aqueous phases were acidified with 6N HCl and extracted with dichloromethane (3×). The combined extracts were dried (Na₂SO₄) and evaporated to give 2-(1'-(tert-butoxycarbonyl)-4-oxo-3,4-dihydro-2H-spiro[naphthalene-1,4'-piperidine]-3-yl)acetic acid 3 as a white solid (1.53 g).

LC-MS: m/e=318.0 (e+), 300.1 (M+H+OC(CH3)3, 100%), 372.4 (M−H, 100%). Rt=3.07 min. 1H NMR (500 MHz, CDCl₃) 7.96 (dd, J=1.4, 7.8 Hz, 1H), 7.50 (td, J=7.8. 1.3 Hz, 1H), 7.41 (d, J=7.8 Hz, 1H), 7.26 (td, J=7.8, 1.0 Hz, 1H), 4.07 (br. t, J=14.3 Hz, 2H), 3.13-3.08 (m, 2H), 2.99 (t, J=13.7 Hz, 2H), 2.64 (dd, J=13.9, 4.2, 1H), 2.42-2.36 (m, 1 H), 2.31 (td, J=13.4, 5.0, 1H), 1.99-1.96 (m, 1H), 1.68-1.61 (m, 2H), 1.42 (s, 9H).

Step 3: (3S,6aR,12a1R)-tert-butyl 5-oxo-3-phenyl-2,3,5,6,6a,7-hexahydrospiro[benzo[g]oxazolo[3,2-i]indole-8,4'-piperidine]-1'-carboxylate

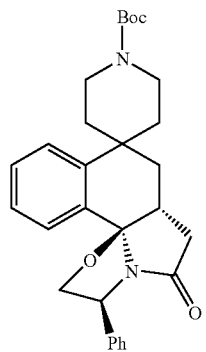

A solution of the acetic acid of Step 2 (1.50 g, 4.0 mmol) and (R)-(−)-2-phenylglycinol (1.2 g, 8.7 mmol) in toluene (100 ml) was refluxed with azeotropic removal of water for 3 days. After evaporation, the residue was purified by silica gel chromatography (CH₂Cl₂/CH₃CN 9:1) to give the title compound as a white solid (1.04 g). LC-MS: m/e 475.2 (M+H, 100%). $R_f$=3.94 min. ¹H-NMR (500 MHz, DMSO-d6): 7.46-7.43 (m, 3H), 7.38-7.35 (m, 3H), 7.27 (t, J=7.5 Hz, 1H), 6.91 (t, J=7.5 Hz, 1H), 6.80 (dd, J=1.1, 7.7 Hz, 1H), 5.13 (t, J=8.3 Hz, 1H, NCHPh), 4.84 (dd, J=8.0, 8.9 Hz, 1H, OCH₂), 3.96 (br. d, J=12.9 Hz, 1H, NCH₂), 3.82 (t, J=9.2 Hz, 1H, OCH₂), 3.76 (br. d, J=11.9 Hz, 1H, NCH₂), 3.17 (m, 1H), 3.11-3.03 (m, 2H), 2.84 (dd, J=5.0, 7.5 Hz, 1H), 2.81 (t, J=9.1 Hz, 1H). 2.62 (dd, J=11.6, 18.6 Hz, 1H), 2.34-2.28 (m, 2H), 1.42 (s, 9H), 1.39-1.35 (m, 1H), 1.31 (td, J=13.3, 4.4 Hz, 1H), 1.12 (t, J=12.6 Hz, 1H). ¹³C-NMR (125 MHz, DMSO-d6): 178.00 (s, NC=O), 153.01 (s, N—COO), 145.50 (s), 137.82 (s), 133.10 (s), 127.58 (d), 127.46 (d), 127.29 (d), 125.99 (d), 125.33 (d), 125.25 (d), 125.15 (d), 124.16 (d), 123.03 (d), 99.03 (s, CCCNO), 77.45 (s, OC(CH₃)₃), 68.69 (t, OCH₂), 57.56 (d, NCH), 40.41-37.96 (multiple t), 37.95 (t), 34.76 (t, COCH₂), 33.63 (s), 26.99 (q, CH₃).

Step 4: (3aR,9bS)-1-((S)-2-hydroxy-1-phenylethyl)-1,3a,4,9b-tetrahydrospiro[benzo[g]indole-5,4'-piperidin]-2(3H)-one

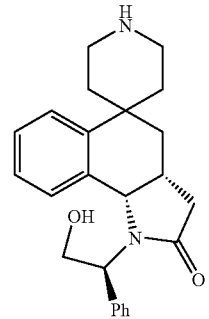

At −78° C., triethylsilane (1.1 ml, 6.9 mmol) was added to a solution of the product of Step 4 (820 mg, 1.73 mmol) in dichloromethane (10 ml) under N₂. After 15 min, a solution of 1 M titanium(IV) chloride in dichloromethane (0.75 ml, 0.75 mmol) was added. The reaction mixture was allowed to warm to room temperature in 5 h, then cooled and quenched with saturated aqueous ammonium chloride. The resulting mixture was basified with 6N NaOH, extracted with EtOAc and then dichloromethane, dried (Na₂SO₄) and evaporate to give (3aR,9bS)-1-((S)-2-hydroxy-1-phenylethyl)-1,3a,4,9b-tetrahydrospiro[benzo[g]indole-5,4'-piperidin]-2(3H)-one 5 (870 mg) as a white solid. LC-MS: m/e=377.2 (100%, M+1). $R_t$=1.83 min. A small amount was purified by reverse phase HPLC to obtained a pure TFA salt. ¹H NMR (500 MHz, DMSO-d6): 7.49 (d, J=7.8 Hz, 1H), 7.44 (t, J=7.8 Hz, 1H), 7.37-7.23 (m, 6H), 6.92 (d, J=7.7 Hz, 1H), 4.56 (d, J=4.6 Hz, 1H, NCH), 4.22 (t, J=6.3 Hz, 1H), 4.15 (dd, J=7.3, 10.7 Hz, 1H), 3.83 (dd, J=5.9, 10.8 Hz, 1H), 3.29 (br. d, J=11.6 Hz, 1H), 3.20-3.09 (m, 3H), 2.83 (dd, J=6.3, 15.7 Hz, 1H), 2.60-2.54 (m, 1H), 2.46-2.42 (m, 1H), 2.29 (dd, J=4.1, 13.9 Hz, 1H), 2.03 (d, J=15.8 Hz, 1H), 1.76 (m, 2H), 1.61 (t, J=13.4 Hz, 1H), 1.52 (d, J=13.5 Hz, 1H).

Step 5: (3aR,9bS)-tert-butyl 1-((S)-2-hydroxy-1-phenylethyl)-2-oxo-1,2,3,3a,4,9b-hexahydrospiro[benzo[g]indole-5,4'-piperidine]-1'-carboxylate

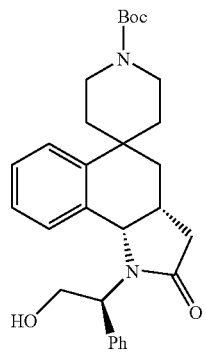

A solution of the product of Step 4 (870 mg, 2.31 mmol) in dichloromethane (30 ml) was treated with Et₃N (0.96 ml, 6.94 mmol) and di-tert-butyl dicarbonate (1.0 g, 0.45 mmol) for 2 h at room temperature. Concentration and the residue was purified by silica gel chromatography (CH₂Cl₂/CH₃CN 7:3) to give (3aR,9bS)-tert-butyl 1-((S)-2-hydroxy-1-phenylethyl)-2-oxo-1,2,3,3a,4,9b-hexahydrospiro[benzo[g]indole-5,4'-piperidine]-1'-carboxylate 6 (550 mg) as a white solid. LC-MS: m/e=477.3 (100% M+1), 421.2 (100%). $R_t$=3.46 min. ¹H NMR (300 MHz, CDCl₃): 7.42-7.24 (m, 5H), 7.13 (d, 2H), 7.07 (t, 1H), 6.75 (d, 1H), 4.50 (d, J=4.9 Hz, 1H), 4.24 (dd, 1H), 4.05-3.91 (m, 3H), 3.82 (dd, 1H), 3.01-2.86 (m, 3H), 2.61-2.51 (m, 1H), 2.29-2.18 (m, 3H), 1.42 (s, 9H), 1.57-1.37 (m, 2H).

Step 6: 1-((S)-2-((3aR,9bS)-1'-(tert-butoxycarbonyl)-2-oxo-2,3,3a,4-tetrahydrospiro[benzo[g]indole-5,4'-piperidine]-1(9bH)-yl)-2-phenylethyl)pyridinium chloride and (3aR,9bS)-tert-butyl 1-((S)-2-chloro-1-phenylethyl)-2-oxo-1,2,3,3a,4,9b-hexahydrospiro[benzo[g]indole-5,4'-piperidine]-1'-carboxylate

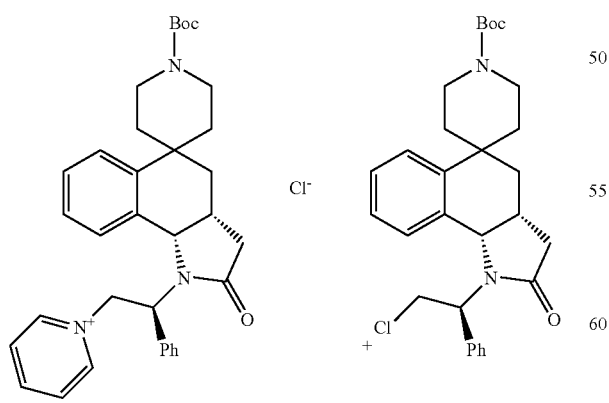

At −10° C., trifluoromethanesulfonic anhydride (0.34 ml, 2 mmol) was added to a solution of pyridine (0.32 ml, 4 mmol) in dichloromethane (15 ml). A white precipitate formed and the mixture was stirred for an additional 10 min. A solution of the 2-phenylethanol of Step 5 (476 mg, 1 mmol) in dichloromethane (10 ml) was added dropwise at −10° C. The reaction mixture was stirred for 2 h, poured into cold sodium bicarbonate aqueous solution and extracted with dichloromethane (3×). The analytical HPLC spectrum of the crude product shows two peaks with a 1:1 ratio (UV-214), which corresponds to the pyridinium salt and starting material. Without purification, the crude mixture was dissolved in dichloromethane (15 ml), treated with triethylamine (0.42 ml, 3 mmol) and methanesulfonyl chloride (0.15 ml, 2 mmol) at room temperature for 4 h. The reaction mixture was diluted with dichloromethane, washed with saturated aqueous ammonium chloride. The organic phase was dried over Na₂SO₄ and concentrated. The residue was purified by flash chromatography (CH₂Cl₂/MeOH 1:0 to 10:4 then to 0:1) to give (3aR,9bS)-tert-butyl 1-((S)-2-chloro-1-phenylethyl)-2-oxo-1,2,3,3a,4,9b-hexahydrospiro[benzo[g]indole-5,4'-piperidine]-1'-carboxylate 8 (350 mg) and 1-((S)-2-((3aR,9bS)-1'-(tert-butoxycarbonyl)-2-oxo-2,3,3a,4-tetrahydrospiro[benzo[g]indole-5,4'-piperidine]-1(9bH)-yl)-2-phenylethyl)pyridinium chloride (186 mg). Data of the pyridinium salt: LC-MS: m/e=538.8 (100%, M+1). $R_t$=2.41 min. ¹H NMR (300 MHz, CDCl₃): 8.69 (d, 2H), 8.33 (t, 1H), 7.75 (t, 2H), 7.65 (d, 2H), 7.53-7.37 (m, 7H), 7.06 (d, 1H), 5.91-5.81 (m, 1H), 5.21-5.12 (m, 2H), 4.49 (d, 1H), 4.00 (d, 1H), 3.93 (d, 1H), 2.91-2.81 (m, 3H), 2.63-2.53 (m, 1H), 2.10 (dd, 1H), 1.50 (m, 4H), 1.49 (s, 9H), 0.67 (d, 1H), 0.47 (t, 1H).

Data of the chloro compound: LC-MS: m/e=439.6 (100%, M+1−t-Bu). $R_t$=3.99 min. ¹H NMR (300 MHz, CDCl₃): 7.53 (d, 1H), 7.46-7.35 (m, 6H), 7.24 (t, 1H), 6.96 (d, 1H), 5.07 (t, 1H), 4.59 (d, 1H), 4.38 (dd, 1H), 4.07 (br. t, 2H), 3.67 (dd, 1H), 3.07-2.97 (m, 2H), 2.85 (dd, 1H), 2.65-2.55 (m, 1H), 2.36-2.22 (m, 3H), 1.94 (t, 1H), 1.61 (m, 3H), 1.51 (s, 9H).

Step 7: (3aR,9bS)-tert-butyl 2-oxo-1-(1-phenylvinyl)-1,2,3,3a,4,9b-hexahydrospiro[benzo[g]indole-5,4'-piperidine]-1'-carboxylate

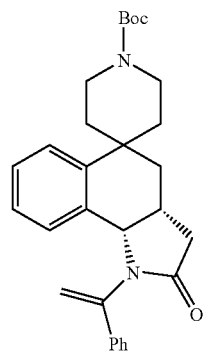

Alternative Method for Preparation of: _(3aR,9bS)-tert-butyl 2-oxo-1-(1-phenylvinyl)-1,2,3,3a,4,9b-hexahydrospiro[benzo[g]indole-5,4'-piperidine]-1'-carboxylate A solution of the alcohol of Step 5 (71.5 mg, 0.15 mmol) in DMSO (5 ml) and lithium hydroxide monohydrate (200 mg) was heated at 170° C. for 8 hours. The solvent was evaporated under high vacuum and the residue was dissolved in water, extracted with dichloromethane. The organic phase was dried (Na₂SO₄), filtered and concentrated to give crude (3aR,9bS)-tert-butyl 2-oxo-1-(1-phenylvinyl)-1,2,3,3a,4,9b-hexahydrospiro[benzo[g]indole-5,4'-piperidine]-1'-carboxylate 9 (69 mg). LC-MS: m/e=459.8 (100%, M⁺). R$_f$=3.68 min. ¹H-NMR (300 MHz, CDCl₃): 7.31-7.14 (m, 7H), 6.90 (t, J=7.5 Hz, 1H), 6.69 (d, J=7.8 Hz, 1H), 5.65 (s, 1H), 4.84 (s, 1H), 4.80 (d, J=5.1 Hz, 1H, NCH), 4.0 (m, 2H), 2.95 (m, 3H), 2.71-2.62 (m, 1H), 2.32-2.23 (m, 3H), 1.61-1.52 (m, 3H), 1.42 (s, 9H), 1.35 (t, 1H).

Step 8: (3aR,9bS)-1,3a,4,9b-tetrahydrospiro[benzo[g]indole-5,4'-piperidin]-2(3H)-one

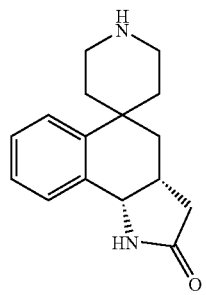

A solution of the Boc-protected indole of Step 7 (69 mg) was heated under reflux with aqueous HCl (6N, 1 ml) in THF (10 ml) for 1 h. Concentration gave the crude (3aR,9bS)-1,3a,4,9b-tetrahydrospiro[benzo[g]indole-5,4'-piperidin]-2(3H)-one.

Alternative preparation of: (3aR,9bS)-1,3a,4,9b-tetrahydrospiro[benzo[g]indole-5,4'-piperidin]-2(3H)-one Step 1: (3aR,9bS)-1-(1-phenylvinyl)-1,3a,4,9b-tetrahydrospiro[benzo[g]indole-5,4'-piperidin]-2(3H)-one

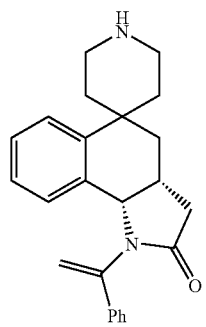

A solution of (3aR,9bS)-1-((S)-2-hydroxy-1-phenylethyl)-1,3a,4,9b-tetrahydrospiro[benzo[g]indole-5,4'-piperidin]-2(3H)-one (Step 4, 2.3 g, 6.1 mmol) and lithium hydroxide monohydrate (2.3 g, 55 mmol) in DMSO (15 ml) was heated at 170° C. for 4 h. The reaction mixture was evaporated. The residue was poured into water, extracted with EtOAc (3×). The extracts were concentrated to give the title compound as brown oil (1.5 g).
LC-MS: m/e=359.6 (100%, M⁺). R$_f$=1.69 min.

Step 2: (3aR,9bS)-1,3a,4,9b-tetrahydrospiro[benzo[g]indole-5,4'-piperidin]-2(3H)-one

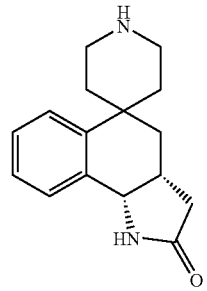

A solution of the crude phenylvinylpyrrolidinone from above (1.5 g) in THF (60 ml) was refluxed with 6N HCl (2 ml) for 1 h. After concentration, the residue was dissolved in brine, basified with 6N NaOH and extracted with dichloromethane (3×). The extracts were dried (Na₂SO₄) and concentrated to give the title pyrrolidinone (900 mg). LC-MS: m/e=257.5 (100%, M⁺). R$_f$=1.65 min.

Preparation 2: 1-((3aR,9bS)-2,3,3a,4-tetrahydrospiro[benzo[g]indole-5,4'-piperidine]-1(9bH)-yl)ethanone

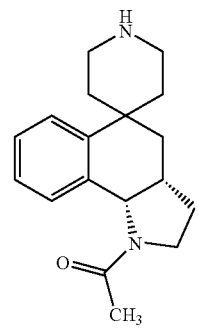

Step 1: (3aR,9bS)-tert-butyl 2-oxo-1,2,3,3a,4,9b-hexahydrospiro[benzo[g]indole-5,4'-piperidine]-1'-carboxylate

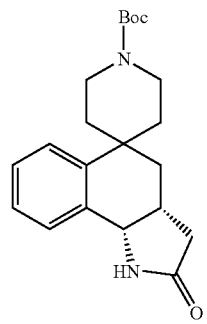

A solution of the (3aR,9bS)-1,3a,4,9b-tetrahydrospiro[benzo[g]indole-5,4'-piperidin]-2(3H)-one (900 mg, 3.51 mmol) in dichloromethane (100 ml) was treated with triethylamine (3 ml) and di-tert-butyl carbonate (1.5 g, 6.8 mmol) at room temperature for 1 h. The reaction mixture was diluted with dichloromethane, washed with aqueous saturated NH₄Cl. The organic phase was separated and the aqueous phase was re-extracted with dichloromethane (2×). The combined organic phases were dried (Na₂SO₄), filtered and concentrated. The residue was purified by flasj chromatography (40 g silica gel, CH₂Cl₂/CH₃CN up to 0:100%) to give (3aR,9bS)-tert-butyl 2-oxo-1,2,3,3a,4,9b-hexahydrospiro[benzo[g]indole-5,4'-piperidine]-1'-carboxylate 12 (700 mg). LC-MS: m/e=301.5 (M−t-Bu+H, 100%). Rt=3.04 min. ¹H NMR (300 MHz, CDCl₃): 7.36 (d, 1H), 7.25 (td, 1H), 7.21-7.13 (m, 2H), 6.32 (s, 1H, NH), 4.71 (d, J=5.8 Hz, 1H, CHN), 4.02 (br. d, 1H), 3.90 (br. d, 1H), 3.01 (td, J=13.4, 2.8 Hz, 1H), 2.89 (td, J=13, 3.1 Hz, 1H), 2.73-2.62 (m, 1H), 2.29 (td, J=12.7, 5.0 Hz, 1H), 2.23-2.44 (m, 3H), 1.66-1.59 (m, 1H), 1.51 (dd, J=13.2, 4.3 Hz, 1H), 1.41 (s, 9H), 1.37-1.30 (m, 2H).

Step 2: (3aR,9bS)-tert-butyl 1,2,3,3a,4,9b-hexahydrospiro[benzo[g]indole-5,4'-piperidine]-1'-carboxylate

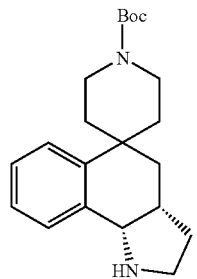

A solution of the 2-oxo-indole of Step 1 (200 mg, 0.56 mmol) in THF (10 ml) and a solution borane-THF complex (1.0M, 5 ml) was heated under reflux for 4 h. The reaction mixture was concentrated. The residue was dissolved in dichloromethane (ca 100 ml), treated with water (ca. 10 ml), 6N HCl (2 ml) then 1N NaOH (3 ml). The organic phase was collected and the aqueous phase was reextracted with dichloromethane. The combined organic phases were dried (Na2SO4), concentrated and purified by flash chromatography (CH₂Cl₂/MeOH up to 4:1) to give (3aR,9bS)-tert-butyl 1,2,3,3a,4,9b-hexahydrospiro[benzo[g]indole-5,4'-piperidine]-1'-carboxylate 13 (52 mg). LC-MS: m/e=343.6 (M+H, 100%). Rt=1.82 min. ¹H-NMR (300 MHz, CDCl₃): 10.46 (m, 1H), 9.36 (m, 1H), 7.56 (d, 1H), 7.34 (d, 1H), 7.27 (t, 1H), 7.12 (t, 1H), 4.35 (m, 1H), 3.93 (t, 2H), 3.18 (m, 2H), 2.87 (q, 2H), 2.49 (m, 1H), 2.34-2.05 (m, 3H), 1.80-1.57 (m, 6H), 1.41 (s, 9H).

Step 3: (3aR,9bS)-tert-butyl 1-acetyl-1,2,3,3a,4,9b-hexahydrospiro[benzo[g]indole-5,4'-piperidine]-1'-carboxylate

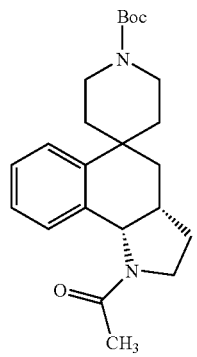

The product of Step 2 (52 mg) was dissolved in dichloromethane (10 ml), treated with triethylamine (0.07 ml) and acetyl chloride (0.014 ml) for 1 h. The reaction mixture was diluted with dichloromethane, washed with water. The organic phase was concentrated to give (3aR,9bS)-tert-butyl 1-acetyl-1,2,3,3a,4,9b-hexahydrospiro[benzo[g]indole-5,4'-piperidine]-1'-carboxylate 14 (47 mg). LC-MS: m/e=329.6 (M+−tBu, 100%). Rt=3.21 min.

Step 4: 1-((3aR,9bS)-2,3,3a,4-tetrahydrospiro[benzo[g]indole-5,4'-piperidine]-1(9bH)-yl)ethanone.

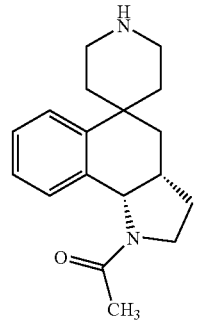

The Boc protecting group of the product of Step 3 (47 mg) was removed by treatment with TFA to give 1-((3aR,9bS)-2,3,3a,4-tetrahydrospiro[benzo[g]indole-5,4'-piperidine]-1(9bH)-yl)ethanone 15 (35 mg). LC-MS: m/e=285.5 (M+, 100%). Rt=1.39 min.

Preparation 3: (3aR,9bS)-1-methyl-1,2,3,3a,4,9b-hexahydrospiro[benzo[g]indole-5,4'-piperidine]

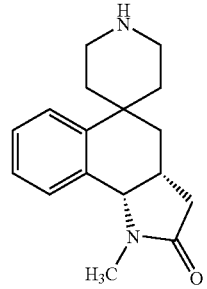

Step 1: (3aR,9bS)-tert-butyl 1-methyl-1,2,3,3a,4,9b-hexahydrospiro[benzo[g]indole-5,4'-piperidine]-1'-carboxylate

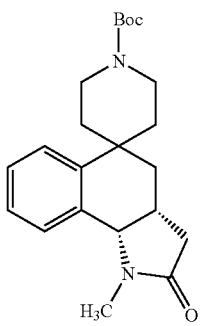

Sodium hydride (60% dispersed in oil, 58 mg) was washed with anhydrous 2,2,4-trimethylpentane and suspended in anhydrous THF. Lithium perchlorate (78 mg, 0.73 mmol) was added to the suspension at 0° C., followed by (3aR,9bS)-tert-butyl 2-oxo-1,2,3,3a,4,9b-hexahydrospiro[benzo[g]indole-5,4'-piperidine]-1'-carboxylate (142 mg, 0.4 mmol) in THF (10 ml) at 0° C. After 15 min, methyl iodide (0.04 ml, 0.6 mmol) was added. The reaction mixture was stirred at room temperature for 1 h then heated under reflux for 1 h. Concentration gave the title compound. LC-MS: m/e=371.6 (M+), 315.5 (M−tBu+1, 100%). Rt=3.12 min.

Step 2: The product of Step 1 was dissolved in dichloromethane (10 ml), treated with TFA (1 ml) at rt for 1 h. The mixture was concentrated and the residue dissolved in dichloromethane. The resulting solution was washed with a mixture of brine and 6N NaOH (1 ml). The aqueous phase was re-extracted with dichloromethane (2×). The combined organic phases were dried (Na$_2$SO$_4$), filtered and concentrated to give (3aR,9bS)-1-methyl-1,3a,4,9b-tetrahydrospiro[benzo[g]indole-5,4'-piperidin]-2(3H)-one 19 (115 mg). LC-MS: m/e=271.5 (M+, 100%). Rt=1.13 min.

Preparation 4: (3aR,9bS)-1-(2-methoxyethyl)-1,3a,4,9b-tetrahydrospiro[benzo[g]indole-5,4'-piperidin]-2(3H)-one The title compound was prepared according to the procedures of Preparation 3.

Step 1 intermediate: (3aR,9bS)-tert-butyl 1-(2-methoxyethyl)-2-oxo-1,2,3,3a,4,9b-hexahydrospiro[benzo[g]indole-5,4'-piperidine]-1'-carboxylate

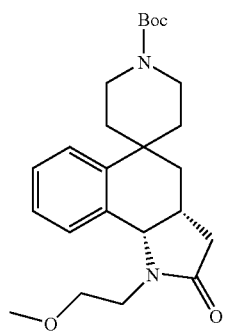

LC-MS: m/e=415.6 (M+, 100%). R$_t$=3.12 ml. $^1$H-NMR (300 MHz, CDCl$_3$): 7.35 (dd, 1H), 7.29 (td, 1H), 7.19 (td, 1H), 6.08 (dd, 1H), 4.54 (d, J=5.4 Hz, 1H), 3.91-3.80 (m, 2H), 3.35-3.20 (m, 3H), 3.15 (t, 1H), 3.11 (s, 3H, OMe), 2.89-2.76 (m, 2H), 2.61 (dd, 1H), 2.47-2.37 (m, 1H), 2.13 (td, 1H), 2.01 (dd, 2H), 1.46 (m, 2H), 1.31 (s, 9H), 1.23 (m, 2H).

Step 2 title compound: LC-MS: m/e=315.5 (M+, 100%). Rt=1.30 min.

Preparation 5: ethyl 2-((3aR,9bS)-2-oxo-2,3,3a,4-tetrahydrospiro[benzo[g]indole-5,4'-piperidine]-1(9bH)-yl)acetate The title compound was prepared according to the procedures of Preparation 3.

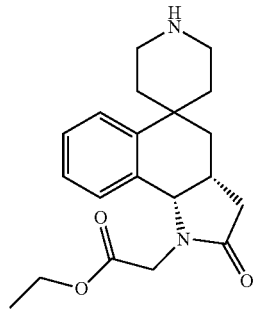

Step 1 intermediate: (3aR,9bS)-tert-butyl 1-(2-ethoxy-2-oxoethyl)-2-oxo-1,2,3,3a,4,9b-hexahydrospiro[benzo[g]indole-5,4'-piperidine]-1'-carboxylate

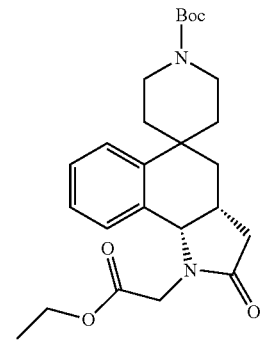

LC-MS: m/e=429.6 (M+), 373.5 (M−tBu+1, 100%). R$_t$=3.12 min. $^1$H-NMR (300 MHz, CDCl$_3$): 7.40 (dd, 1H), 7.29 (td, 1H), 7.15 (td, 1H), 6.99 (dd, 1H), 4.69 (d, J=5.29 Hz, 1H), 4.21 (d, 1H), 4.04-3.90 (m, 2H), 3.66 (d, 1H), 3.58 (s, 3H, OMe), 3.00-2.86 (m, 2H), 2.84 (d, 1H), 2.78 (dd, 1H), 2.64-2.54 (m, 1H), 2.24 (td, 1H), 2.15 (d, 1H), 2.14 (dd, 1H), 1.62-1.48 (m, 3H), 1.42 (s, 9H).

Step 2 title compound: LC-MS: m/e=329.5 (M+, 100%). R$_t$=1.30 min.

Preparation 6: 3,3a,4,9b-tetrahydro-2H-spiro[naphtho[1,2-b]furan-5,4'-piperidin]-2-one

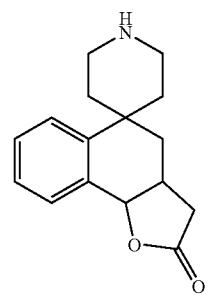

51

Step 1: tert-butyl 2-oxo-3,3a,4,9b-tetrahydro-2H-spiro[naphtho[1,2-b]furan-5,4'-piperidine]-1'-carboxylate

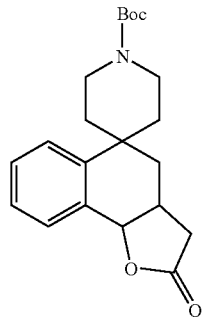

Zn(BH$_4$)$_2$ was prepared following a known procedure (Beatrix Merla, Hans-Joachim Grumbach, Nikolaus Risch, Synthesis, 1998 1609-1614). At 0° C., zinc chloride (anhydrous, 5 g, 36.6 mmol) was added to a solution of sodium borohydride (2.72 g, 72 mmol) in diethyl ether (100 ml). The reaction mixture was stirred at 0° C. for 2 h. After filtration under N$_2$, the borohydride solution (9 ml) was added to a suspension of the tert-butyl 3-(2-methoxy-2-oxoethyl)-4-oxo-3,4-dihydro-2H-spiro[naphthalene-1,4'-piperidine]-1'-carboxylate (589 mg, 1.52 mmol). After 1 h, additional borohydride solution (9 ml) was added and the mixture stirred for 15 h. The mixture was quenched with 1N HCl, neutralized with saturated sodium bicarbonate, extracted with EtOAc. The extract was concentrated and the residue purified by flash chromatography to give the title compound (140 mg).

LC-MS: m/e=302.43 (M$^+$−tBu+1), 258.4 (M−Boc+1, 100%). R$_t$=3.40 min. $^1$H-NMR (300 MHz, CDCl$_3$): 7.32 (dd, 1H), 7.30 (dd, 1H), 7.25 (td, 1H), 7.16 (td, 1H), 4.88 (d, J=10.6 Hz, 1H), 4.02 (m, 2H), 2.93 (td, 1H), 2.82 (td, 1H), 2.64 (dd, 1H), 2.51 (dd, 1H), 2.31-2.16 (m, 1H), 1.99 (td, 1H), 1.88 (td, 1H), 1.68-1.54 (m, 1H), 1.42 (s, 9H), 1.50-1.39 (m, 2H).

Step 2: 3,3a,4,9b-tetrahydro-2H-spiro[naphtho[1,2-b]furan-5,4'-piperidin]-2-one

The Boc protecting group of the product of Step 1 (140 mg) was removed by treatment with TFA (1 ml) in dichlormethane (5 ml) for 3 hr at room temperature to give the title compound. LC-MS: m/e=258.4 (M$^+$, 100%). R$_t$=1.30 min.

Preparation 7: 3,3a,4,9b-tetrahydro-2H-spiro[naphtho[1,2-b]furan-5,4'-piperidine]

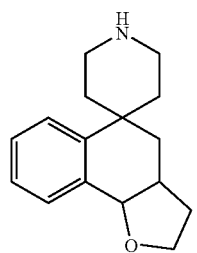

52

Step 1: tert-butyl 4-hydroxy-3-(2-hydroxyethyl)-3,4-dihydro-2H-spiro[naphthalene-1,4'-piperidine]-1'-carboxylate

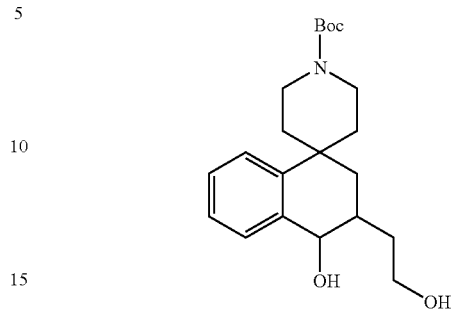

A powder of lithium borohydride (84 mg, 4 mmol) was added to a solution of tert-butyl 3-(2-methoxy-2-oxoethyl)-4-oxo-3,4-dihydro-2H-spiro[naphthalene-1,4'-piperidine]-1'-carboxylate (140 mg, 0.36 mmol) and the mixture stirred at room temperature for 15 h. Then MeOH and 1N HCl (1 ml) was added. The mixture was concentrated and the residue was suspended in brine, extracted with EtOAc (3×). The extracts were dried (Na$_2$SO$_4$), filtered and concentrated. The residue was purified by flash chromatography (CH$_2$Cl$_2$/CH$_3$CN up to 6:4) to give the diol product (90 mg).

Step 2: 3,3a,4,9b-tetrahydro-2H-spiro[naphtho[1,2-b]furan-5,4'-piperidine]

At −60° C., BF$_3$OEt$_2$ was added to a solution of the diol product of Step 1 (90 mg, 0.25 mmol) in dichloromethane (15 ml). After the addition, the reaction mixture was allowed to warm to room temperature, kept overnight, diluted with dichloromethane, then washed with saturated sodium bicarbonate. The aqueous phase was extracted with dichloromethane (2×). The combined extracts were dried (Na$_2$SO$_4$) and concentrated to give the title compound tert-butyl 3,3a,4,9b-tetrahydro-2H-spiro[naphtho[1,2-b]furan-5,4'-piperidine]-1'-carboxylate (53 mg). LC-MS: m/e=244.4 (M$^+$, 100%). R$_t$=1.22 min. $^1$H-NMR (300 MHz, CDCl$_3$): 7.40 (dd, 1H), 7.37 (dd, 1H), 7.23 (td, 1H), 7.15 (td, 1H), 4.56 (d, J=5.4 Hz, 1H), 3.93 (q, 1H), 3.80 (td, 1H), 3.58 (m, 1H), 2.98 (m, 3H), 2.49-2.18 (m, 4H), 1.72-1.52 (m, 3H), 1.44-1.13 (m, 3H).

Example 1

1'-cyclohexyl-1,3a,4,9b-tetrahydrospiro[benzo[g]indole-5,4'-piperidin]-2(3H)-one

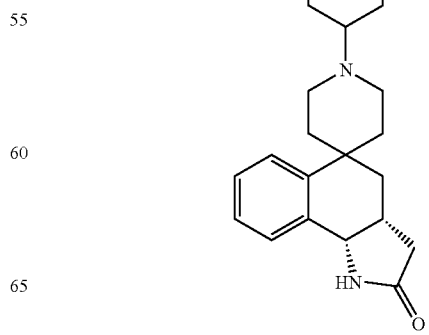

To a solution of (3aR,9bS)-1,3a,4,9b-tetrahydrospiro[benzo[g]indole-5,4'-piperidin]-2(3H)-one (22 mg) and cyclohexanone (36 mg) in 1,2-dichloroethane (2 ml) was added titanium isopropoxide (0.05 ml) and the resulting solution was stirred at 40° C. for 3 h, then treated with sodium triacetoxyborohydride (50 mg) for 3 h, cooled to room temperature. The reaction mixture was diluted to 5 ml with dichloromethane, then treated with a mixture of brine and 6N NaOH. The organic layer was separated and concentrated. The residue was dissolved in MeOH (1 ml) and purified by reverse phase HPLC to give (3aR,9bS)-1'-cyclohexyl-1,3a,4,9b-tetrahydrospiro[benzo[g]indole-5,4'-piperidin]-2(3H)-one as a TFA salt.

A person skilled in the chemical arts can use the examples and schemes along with known synthetic methodologies to synthesize compounds of the present invention, including the compounds in Table 2 below.

TABLE 2

Physical data for exemplary compounds.

| Compound No. | LC/MS M + 1 | LC/RT min | NMR |
|---|---|---|---|
| 1 | 470.6 | 1.52 | 300 MHz, DMSO-d6: 9.44 (m, 1H), 7.52 (d, 1H), 7.50 (d, 1H), 7.44 (t, 1H), 7.31 (t, 1H), 4.62 (d, J = 4.7 Hz, 1H), 4.12 (m, 2H), 4.05 (q, 2H), 3.48-3.02 (m, 8H), 3.11 (s, 3H), 2.82 (m, 2H), 2.70 (dd, 1H), 2.60 (m, 2H), 2.36 (t, 1H), 2.28 (dd, 1H), 2.08 (m, 2H), 1.94 (d, 1H), 1.88 (m, 2H), 1.56 (m, 3H), 1.30 (t, 1H), 1.19 (t, 3H). |
| 2 | 399.6 | 1.61 | 300 MHz, DMSO-d6: 9.38 (m, 1H), 7.39-7.31 (m, 3H), 7.25 (td, 1H), 4.55 (d, J = 5.5 Hz, 1H), 4.16-4.09 (m, 2H), 4.05 (q, 2H), 3.86 (q, 1H), 3.75 (td, 1H), 3.65 (t, 1H), 3.52-3.17 (m, 5H), 2.82 (br. t, 2H), 2.68 (td, 1H), 2.39-2.23 (m, 3H), 2.10 (m, 2H), 1.94 (d, 1H), 1.79-1.52 (m, 5H), 1.20 (t, 3H). |
| 3 | 379.7 | 1.78 | 300 MHz, DMSO-d6: 9.06 (m, 1H), 7.48-7.40 (m, 3H), 7.31 (ddd, 1H), 4.47 (d, 1H), 3.46-3.32 (m, 3H), 3.17-3.02 (m, 2H), 2.73-2.56 (m, 3H), 2.62 (s, 3H), 2.44-2.24 (m, 5H), 1.96 (d, 2H), 1.83-1.63 (m, 4H), 1.59-1.19 (m, 7H), 1.01 (td, 1H). |
| 4 | 413.6 | 1.56 | 300 MHz, DMSO-d6: 9.50 (m, 1H), 7.47 (d, 1H), 7.39 (ddd, 1H), 7.28 (t, 1H), 7.27 (t, 1H), 5.10 (d, J = 10.9 Hz, 1H), 4.13 (m, 2H), 4.06 (q, 2H), 3.44 (q, 3H), 3.29 (q, 1H), 3.10 (q, 1H), 3.83 (m, 2H), 2.61 (td, 1H), 2.56 (dd, 2H), 2.33-2.05 (m, 5H), 1.92 (d, 1H), 1.79 (d, 1H), 1.66-1.54 (m, 3H), 1.20 (t, 3H). |
| 5 | 365.6 | 1.61 | 300 MHz, DMSO-d6: 9.34 (m, 1H), 8.03 (s, 1H), 7.40-7.22 (m, 4H), 4.64 (d, 1H), 3.48-3.31 (m, 3H), 3.17-3.05 (m, 2H), 2.66 (m, 3H), 2.34 (m, 4H), 1.98-1.63 (m, 5H), 1.56-1.30 (m, 6H), 1.20 (t, 1H), 1.00 (d, 1H). |
| 6 | 338.6 | 1.65 | 300 MHz, DMSO-d6: 8.67 (m, 1H), 7.41-7.32 (m, 3H), 7.24 (td, 1H), 4.54 (d, J = 5.5 Hz, 1H), 3.86 (q, 1H), 3.75 (td, 1H), 3.23 (m, 5H), 2.77 (td, 1H), 2.6 (m, 1H), 2.39-2.26 (m, 3H), 2.07-1.49 (m, 9H), 1.41 (m, 3H), 1.20 (m, 1H), 1.14 (t, 1H). |
| 7 | 339.6 | 1.48 | 300 MHz, DMSO-d6: 9.36 (m, 1H), 8.08 (s, 1H), 7.45-7.22 (m, 4H), 4.63 (d, 1H), 3.45-3.18 (m, 4H), 2.80-2.65 (m, 2H), 2.35 (d, 1H), 2.25 (t, 1H), 2.10 (m, 2H), 1.93-1.09 (m, 14H). |
| 8 | 352.6 | 1.78 | — |
| 9 | 412.6 | 1.46 | 300 MHz, DMSO-d6: 9.73 (m, 1H), 8.08 (s, 1H), 7.41 (d, 1H), 7.32 (m, 2H), 7.24 (t, 1H), 4.64 (d, 1H), 4.12 (m, 4H), 4.05 (q, 2H), 3.48-3.18 (m, 5H), 2.85-2.65 (m, 5H), 2.10 (m, 2H), 1.96-1.78 (m, 3H), 1.59 (m, 3H), 1.19 (t, 3H). |
| 10 | 367.7 | 1.61 | 300 MHz, DMSO-d6: 8.99 (m, 1H), 7.50 (d, 1H), 7.44 (td, 1H), 7.43 (dd, 1H), 7.31 (dd, 1H), 4.46 (d, 1H), 3.35-3.15 (m, 5H), 2.73-2.55 (m, 3H), 2.62 (s, 3H), 2.31 (dd, 1H), 2.10-1.98 (m, 4H), 1.89 (m, 2H), 1.77-1.68 (m, 4H), 1.58-1.46 (m, 6H), 1.21 (t, 1H). |
| 11 | 340.6 | 1.78 | — |
| 12 | 426.7 | 1.56 | 300 MHz, DMSO-d6: 9.41 (m, 1H), 7.50-7.41 (m, 3H), 7.31 (ddd, 1H), 4.47 (d, 1H), 4.12 (m, 2H), 4.05 (q, 2H), 3.47-3.14 (m, 5H), 2.86-2.58 (m, 4H), 2.62 (s, 3H), 2.29 (dd, 1H), 2.08 (m, 2H), 1.97 (d, 1H), 1.90-1.79 (m, 2H), 1.58 (m, 3H), 1.19 (t, 3H). |
| 13 | 470.6 | 1.42 | 300 MHz, DMSO-d6: 12.7 (m, 1H), 9.28 (m, 1H), 7.54 (d, 1H), 7.45 (t, 1H), 7.34 (t, 1H), 7.25 (d, 1H), 4.71 (d, J = 4.5 Hz, 1H), 4.17 (m, 4H), 4.06 (q, 2H), 3.53-3.19 (m, 5H), 3.06 (ddd, 2H), 2.92-2.65 (m, 4H), 2.35 (dd, 1H), 2.14 |

TABLE 2-continued

Physical data for exemplary compounds.

| Compound No. | LC/MS M + 1 | LC/RT min | NMR |
|---|---|---|---|
| 14 | 340.5 | 1.78 | (m, 1H), 1.95 (m, 2H), 1.77-1.62 (m, 5H), 1.49 (t, 1H), 1.21 (t, 3H). 300 MHz, DMSO-d6: 8.89 (m, 1H), 7.40-7.31 (m, 3H), 7.24 (td, 1H), 4.54 (d, J = 5.5 Hz, 1H), 3.87 (q, 1H), 3.75 (td, 1H), 3.48 (br.d, 1H), 3.36 (br. d, 1H), 3.29-3.11 (m, 2H), 3.01 (t, 2H), 2.73 (td, 1H), 2.39-2.34 (m, 2H), 1.91-1.49 (d, 10H), 1.34-0.93 (m, 7H) |
| 15 | 379.7 | 1.78 | 300 MHz, DMSO-d6: 8.89 (m, 1H), 7.47-7.40 (m, 3H), 7.33-7.28 (m, 1H), 4.47 (d, 1H), 3.5 (m, 3H, buried in H2O signal), 3.17-3.06 (m, 2H), 2.73-2.56 (m, 3H), 2.62 (s, 3H), 2.44-2.24 (m, 5H), 1.96 (d, 2H), 1.83-1.63 (m, 4H), 1.59-1.19 (m, 7H), 1.01 (td, 1H). |
| 16 | 397.6 | 1.56 | 300 MHz, DMSO-d6: 9.14 (m, 1H), 7.52 (d, 1H), 7.51 (d, 1H), 7.45 (t, 1H), 7.31 (t, 1H), 4.62 (d, J = 5.2 Hz, 1H), 3.43-3.02 (m, 9H), 3.10 (s, 3H), 2.74-2.53 (m, 3H), 2.30-2.22 (m, 1H), 2.09 (m, 2H), 1.96 (d, 1H), 1.87 (m, 4H), 1.65-1.06 (m, 8H). |
| 17 | 412.7 | 1.95 | — |
| 18 | 354.6 | 1.78 | 300 MHz, DMSO-d6: 9.02 (m, 1H), 7.50 (d, 1H), 7.40 (ddd, 1H), 7.28 (t, 1H), 7.27 (d, 1H), 5.10 (d, J = 10.9 Hz, 1H), 3.45 (br.d, 2H), 3.29-3.04 (m, 2H), 3.00 (t, 2H), 2.62 (td, 1H), 2.56 (dd, 2H), 2.41 (td, 1H), 2.33-2.14 (m, 3H), 1.89-1.55 (m, 4H), 1.38-1.14 (m, 7H), 0.99 (q, 2H). |
| 19 | 339.6 | 2.04 | — |
| 20 | 426.7 | 1.65 | 300 MHz, DMSO-d6: 9.45 (m, 1H), 7.49 (d, 1H), 7.44 (d, 1H), 7.43 (t, 1H), 7.31 (ddd, 1H), 4.47 (d, 1H), 4.12 (m, 2H), 4.05 (q, 2H), 3.46-3.14 (m, 5H), 2.82 (t, 1H), 2.73-2.57 (m, 3H), 2.62 (s, 3H), 2.29 (dd, 1H), 2.08 (m, 2H), 1.98 (d, 1H), 1.90-1.79 (m, 2H), 1.58 (m, 3H), 1.19 (t, 3H). |
| 21 | 340.5 | 1.56 | 300 MHz, DMSO-d6: 9.31 (m, 1H), 7.50 (d, 1H), 7.39 (ddd, 1H), 7.28 (t, 1H), 7.27 (t, 1H), 5.10 (d, J = 10.9 Hz, 1H), 3.44-3.03 (m, 5H), 2.67-2.52 (m, 3H), 2.43-2.06 (m, 5H), 1.93-1.76 (m, 4H), 1.66-1.06 (m, 7H). |
| 22 | 411.6 | 1.74 | 300 MHz, DMSO-d6: 8.93 (m, 1H), 7.52 (br.d, 2H), 7.44 (t, 1H), 7.31 (t, 1H), 4.62 (d, J = 4.5 Hz, 1H), 3.47-2.93 (m, 10H), 3.11 (s, 3H), 2.76-2.56 (m, 3H), 2.30 (dd, 1H), 1.92 (d, 1H), 1.88-1.47 (m, 7H), 1.33-1.14 (m, 6H), 0.98 (q, 2H). |
| 23 | 353.6 | 1.56 | 300 MHz, DMSO-d6: 9.01 (m, 1H), 7.50 (d, 1H), 7.46-7.41 (m, 2H), 7.30 (t, 1H), 4.47 (d, 1H), 3.44-3.16 (m, 5H), 2.72-2.58 (m, 3H), 2.62 (s, 3H), 2.29 (dd, 1H), 2.08 (m, 2H), 1.98 (d, 1H), 1.98 (m, 4H), 1.61 (t, 2H), 1.49-1.10 (m, 6H). |
| 24 | 353.7 | 1.61 | 300 MHz, DMSO-d6: 9.06 (m, 1H), 7.52-7.41 (m, 3H), 7.31 (ddd, 1H), 4.47 (d, 1H), 3.40-3.13 (m, 5H), 2.72-2.58 (m, 3H), 2.62 (s, 3H), 2.29 (dd, 1H), 2.07 (m, 2H), 1.98 (d, 1H), 1.90-1.83 (m, 4H), 1.74-1.60 (m, 2H), 1.48-1.06 (m, 6H). |
| 25 | 363.6 | 2 | — |
| 26 | 326.6 | 1.65 | 300 MHz, DMSO-d6: 8.98 (m, 1H), 7.40-7.32 (m, 3H), 7.24 (td, 1H), 4.54 (d, J = 5.6 Hz, 1H), 3.85 (q, 1H), 3.75 (td, 1H), 3.25 (m, 3H), 2.70 (m, 1H), 2.38-2.23 (m, 3H), 2.10 (m, 2H), 1.95-1.09 (m, 15H). |
| 27 | 367.7 | 1.69 | — |
| 28 | 366.6 | 1.74 | — |
| 29 | 367.7 | 1.74 | 300 MHz, DMSO-d6: 9.15 (m, 1H), 7.51 (d, 1H), 7.46-7.41 (m, 2H), 7.30 (dd, 1H), 4.46 (d, 1H), 3.44-3.15 (m, 5H), 2.71-2.54 (m, 3H), 2.62 (s, 3H), 2.29 (dd, 1H), 2.06 (m, 3H), 2.00 (d, 1H), 1.89 (m, 2H), 1.77-1.66 (m, 4H), 1.58-1.46 (m, 6H), 1.21 (t, 1H). |
| 30 | 351.5 | 1.95 | — |
| 31 | 325.5 | 1.65 | — |
| 32 | 337.5 | 1.74 | — |

VI. Assays for Detecting and Measuring Inhibition Properties of Compounds

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12430-054), containing 25 mM Hepes and supplemented with Fetal Bovine Serum (Hyclone, cat #SH30071.03), 0.1 mM of MEM non-essential amino acids (GIBCO, Cat #11140-050), 1 mM MEM Sodium Pyruvate (GIBCO Cat #11360-070) and 100 units/ml of Penicillin G and 100 μg/ml of Streptomycin (GIBCO Cat #15140-122). The recombinant muscarinic receptor cell lines are grown under antibiotic pressure with media containing 25 μg/ml zeocin and 500 μg/ml G418 (M1-CHO), 4 μg/ml puromycin, 50 μg/ml zeocin and 2.5 μg/ml blasticidin (M2 and M4-CHO) or 50 μg/ml zeocin and 4 μg/ml puromycin (M3 and M5-CHO).

Cells are harvested at 80-90% confluence using Versene (GIBCO Cat #15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 μl/well of Fluo-3 AM at 4 μM, Molecular Probes F-1241, in Bath 1 buffer containing 1 mM Probenecid) is added to the 25 μl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 μl/well of this solution after the wash. Alternatively, cells can be loaded with the calcium indicator from Molecular Devices (Calcium 3 Assay Reagents, Cat #R7181) adding 5 μl of a 5× solution dye in Bath 1 containing 1 mM Probenecid (10 ml per dye flask cat #R7182 to generate a solution 20×) to 20 μl of the same buffer. After loading for 60 min, the experiment can be run without having to remove the dye.

Compounds are prepared at a 2× fold concentration in a 96-well plate (round bottom, Costar Corning cat #3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 μl compound/well) to the cell assay plate (containing 25 μl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 μl compound/well) to the assay plate and pre-incubated for 15 min prior to adding 25 μl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on M4 receptors.

The compounds of the present invention were found to modulate the $M_1$ and/or $M_4$ muscarinic receptors selectively over the other receptor types.

Examples of activities and efficacies of the muscarinic compounds of formulae (I, Ia, and Ib) on modulating $M_1$ and $M_4$ receptors are shown below in Table 3. The compound activity for the $M_1$, $M_2$, $M_3$ and $M_4$ is illustrated with "+++" if activity was measured to be less than 2.0 μM, "++" if activity was measured to be from 2.0 μM to 5.0 μM, "+" if activity was measured to be greater than 5.0 μM, and "−" if no data was available. The efficacy for $M_1$ and $M_4$ modulation is illustrated with "+++" if efficacy was calculated to be greater than 100%, "++" if efficacy was calculated to be from 100% to 25%, "+" if efficacy was calculated to be less than 25%, and "−" if no data was available. It should be noted that 100% efficacy is the maximum response obtained with the Carbachol control.

TABLE 3

Compound activities and efficacies for modulating $M_1$ and $M_4$ receptors.

| Compound No. | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 1  | +++ | ++ | +++ | ++ | +   | +   | +++ | ++ |
| 2  | +++ | ++ | +++ | ++ | +   | +   | +++ | ++ |
| 3  | +++ | ++ | +++ | +  | +   | +   | +++ | ++ |
| 4  | +++ | ++ | +++ | ++ | +   | ++  | +++ | ++ |
| 5  | +++ | ++ | +++ | ++ | +   | +   | +++ | ++ |
| 6  | +   | +  | +   | +  | +   | +   | +++ | ++ |
| 7  | +++ | ++ | +++ | ++ | +   | +   | +++ | ++ |
| 8  | +   | ++ | +   | +  | +   | +   | +++ | ++ |
| 9  | +++ | ++ | +++ | ++ | +++ | ++  | +++ | ++ |
| 10 | ++  | ++ | +   | ++ | +   | +   | +++ | ++ |
| 11 | ++  | ++ | +   | +  | +   | +   | +++ | ++ |
| 12 | +++ | ++ | +++ | ++ | +   | +   | +++ | ++ |
| 13 | +   | ++ | +   | +  | +   | +   | +   | ++ |
| 14 | +   | ++ | +   | +  | +   | +   | +++ | ++ |
| 15 | ++  | ++ | +   | +  | +   | +   | +++ | ++ |
| 16 | +   | +  | +   | +  | +   | +   | +++ | ++ |
| 17 | +++ | ++ | +++ | ++ | +   | +   | +++ | ++ |
| 18 | +++ | ++ | +   | ++ | +   | +   | +++ | ++ |
| 19 | +++ | ++ | ++  | ++ | +   | +   | +++ | ++ |
| 20 | +++ | ++ | +++ | ++ | +   | +   | +++ | ++ |
| 21 | +++ | ++ | +   | ++ | +   | +   | +++ | ++ |
| 22 | ++  | ++ | +   | +  | +   | +   | +++ | ++ |
| 23 | +++ | ++ | +++ | ++ | +   | +   | +++ | ++ |
| 24 | +   | ++ | +   | +  | +   | +   | +++ | ++ |
| 25 | +++ | ++ | +++ | ++ | +   | ++  | +++ | ++ |
| 26 | +   | ++ | +   | +  | +   | +   | +++ | +  |
| 27 | +   | +  | +   | +  | +   | +   | +   | +  |

TABLE 3-continued

Compound activities and efficacies for modulating $M_1$ and $M_4$ receptors.

| Compound No. | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 28 | +++ | ++ | + | + | + | + | +++ | ++ |
| 29 | +++ | ++ | +++ | ++ | + | + | +++ | ++ |
| 30 | +++ | ++ | ++ | ++ | + | + | +++ | ++ |
| 31 | +++ | ++ | ++ | + | + | + | +++ | ++ |
| 32 | ++ | ++ | ++ | ++ | + | + | +++ | ++ |

VII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula I:

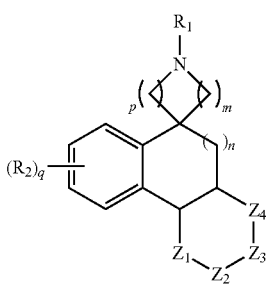

I or a pharmaceutically acceptable salt thereof, wherein
$R_1$ is —$Z^A R_4$, wherein $Z^A$ is independently a bond or —$CH_2$—;
Each $R_4$ is independently $R^A$, halo, —OH, —$NH_2$, —$NO_2$, —CN, or —$OCF_3$;
Each $R^A$ is independently a cycloaliphatic or heterocycloaliphatic, each of which is optionally substituted;
Each $R_2$ is hydrogen;
$Z_1, Z_2, Z_3,$ and $Z_4$ together with the atoms to which they are attached form

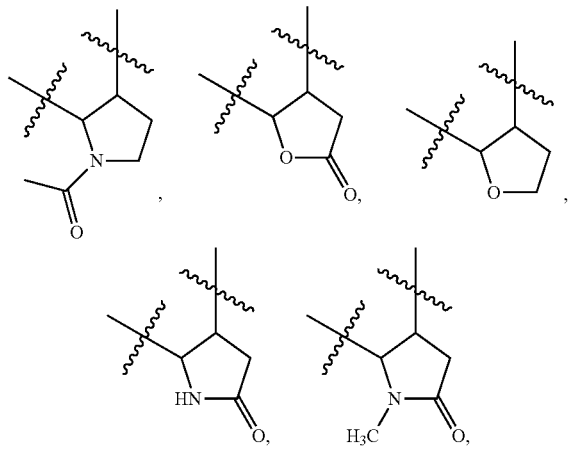

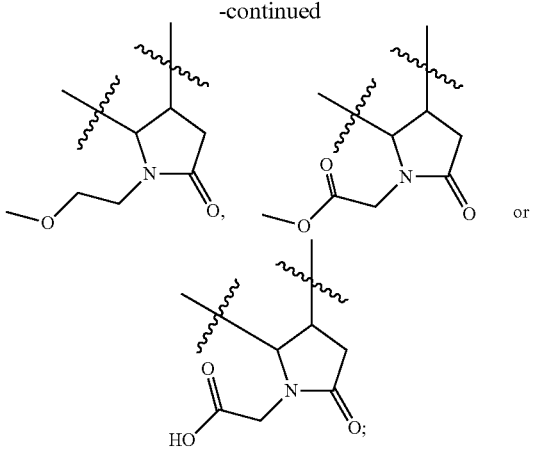

p is 2;
m is 2;
n is 0 or 1; and
q is 0-4.

2. The compound of claim 1, wherein $R_1$ is —$Z^A R_4$, $Z^A$ is —$CH_2$—, and $R_4$ is an optionally substituted cycloaliphatic or an optionally substituted heterocycloaliphatic.

3. The compound of claim 2, wherein $R_1$ is —$Z^A R_4$, $Z^A$ is —$CH_2$—, and $R_4$ is an optionally substituted monocyclic cycloaliphatic or an optionally substituted bicyclic cycloaliphatic.

4. The compound of claim 3, wherein $R_1$ is —$Z^A R_4$, $Z^A$ is —$CH_2$—, and $R_4$ is a 3-7 membered monocyclic cycloalkyl or a 3-7 membered monocyclic cycloalkenyl, either of which is optionally substituted.

5. The compound of claim 4, wherein $R_1$ is —$Z^A R_4$, $Z^A$ is —$CH_2$—, and $R_4$ is an optionally substituted 3-7 membered monocyclic cycloalkyl.

6. The compound of claim 3, wherein $R_1$ is —$Z^A R_4$, $Z^A$ is —$CH_2$—, and $R_4$ is an optionally substituted bicyclic cycloaliphatic.

7. The compound of claim 6, wherein $R_1$ is —$Z^A R_4$, $Z^A$ is —$CH_2$—, and $R_4$ is an optionally substituted bicyclic cycloalkyl or an optionally substituted bicyclic cycloalkenyl.

8. The compound of claim 7, wherein $R_1$ is —$Z^A R_4$, $Z^A$ is —$CH_2$—, and $R_4$ is an optionally substituted 5-10 membered bicyclic cycloalkyl.

9. The compound of claim 7, wherein $R_1$ is —$Z^A R_4$, wherein $Z^A$ is —$CH_2$—, and $R_4$ is an optionally substituted 7-10 membered bicyclic cycloalkenyl.

10. The compound of claim 1, wherein $R_1$ is —$Z^A R_4$, wherein $Z^A$ is a bond, and $R_4$ is an optionally substituted cycloaliphatic or an optionally substituted heterocycloaliphatic.

11. The compound of claim 10, wherein $R_1$ is —$Z^A R_4$, $Z^A$ is a bond, and $R_4$ is an optionally substituted monocyclic cycloaliphatic or an optionally substituted bicyclic cycloaliphatic.

12. The compound of claim 11, wherein $R_1$ is $—Z^A R_4$, $Z^A$ is a bond, and $R_4$ is a 3-7 membered monocyclic cycloalkyl or cycloalkenyl, either of which is optionally substituted.

13. The compound of claim 12, wherein $R_1$ is $—Z^A R_4$, $Z^A$ is a bond, and $R_4$ is an optionally substituted 3-7 membered optionally substituted monocyclic cycloalkyl.

14. The compound of claim 11, wherein $R_1$ is $—Z^A R_4$, $Z^A$ is a bond, and $R_4$ is an optionally substituted bicyclic cycloaliphatic.

15. The compound of claim 14, wherein $R_1$ is $—Z^A R_4$, $Z^A$ is a bond, and $R_4$ is an optionally substituted bicyclic cycloalkyl or an optionally substituted bicyclic cycloalkenyl.

16. The compound of claim 15, wherein $R_1$ is $—Z^A R_4$, $Z^A$ is a bond, and $R_4$ is bicyclo[1.1.1]pentane-yl, bicyclo[2.1.1]hexane-yl, bicyclo[2.2.1]heptane-yl, bicyclo[2.2.2]octane-yl, bicyclo[3.1.1]heptane-yl, bicyclo[3.2.1]octane-yl, bicyclo[3.3.2]decane-yl, bicyclo[2.2.1]hept-en-yl, bicyclo[2.2.2]oct-en-yl, bicyclo[3.2.1]oct-en-yl, or bicyclo[3.3.2]dec-en-yl, each of which is optionally substituted.

17. The compound of claim 2, wherein $R_1$ is $—Z^A R_4$, $Z^A$ is $—CH_2—$, and $R_4$ is an optionally substituted heterocycloaliphatic.

18. The compound of claim 17, wherein $R_1$ is $—Z^A R_4$, $Z^A$ is $—CH_2—$, and $R_4$ is an optionally substituted monocyclic or bicyclic heterocycloaliphatic.

19. The compound of claim 18, wherein $R_1$ is $—Z^A R_4$, $Z^A$ is $—CH_2—$, and $R_4$ is an optionally substituted monocyclic 5-8 membered heterocycloaliphatic having 1-3 heteroatoms independently selected from N, O, and S.

20. The compound of claim 10, wherein $R_1$ is $—Z^A R_4$, $Z^A$ is a bond, and $R_4$ is an optionally substituted heterocycloaliphatic.

21. The compound of claim 20, wherein $R_1$ is $—Z^A R_4$, $Z^A$ is a bond, and $R_4$ is an optionally substituted 5-10 membered optionally substituted monocyclic or bicyclic heterocycloaliphatic having 1-3 heteroatoms independently selected from N, O, and S.

22. The compound of claim 1, wherein $R_1$ is one selected from:

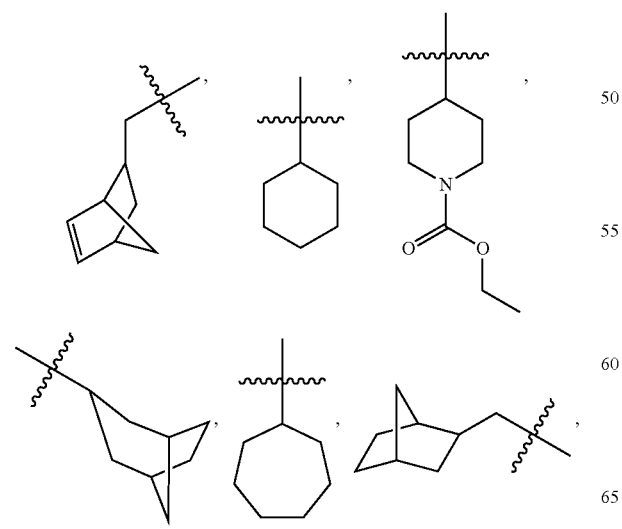

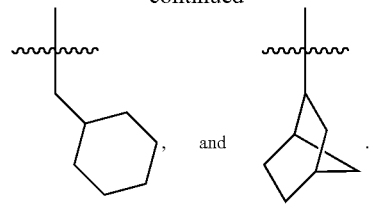

23. A pharmaceutical composition comprising a compound according to claim 1 and a pharmaceutical carrier.

24. A compound selected from:

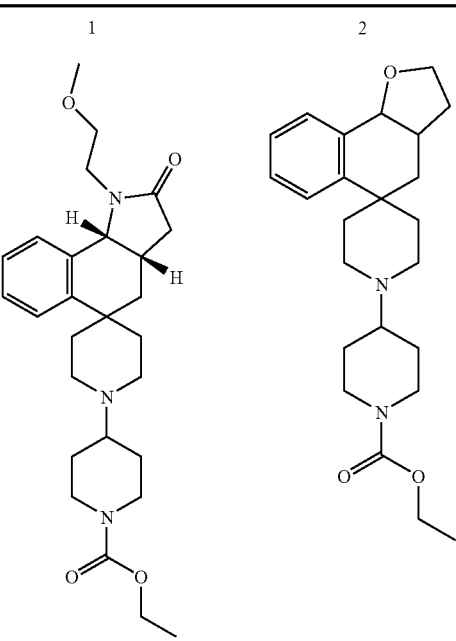

-continued
| 5 | 6 | 11 | 12 |
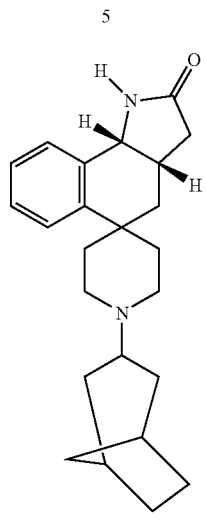 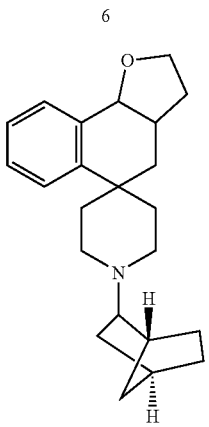 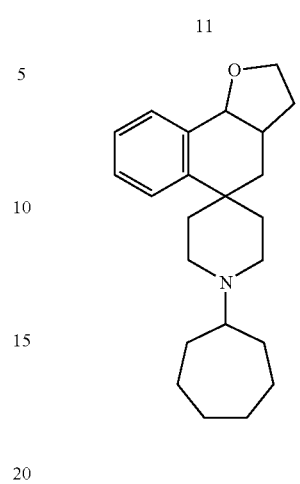 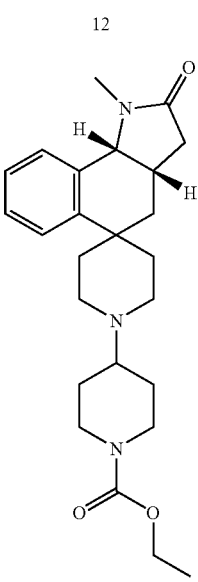
| 7 | 8 |
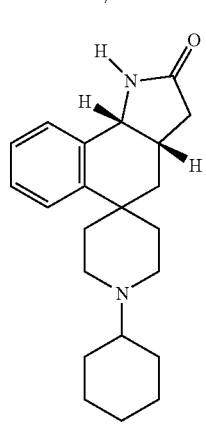 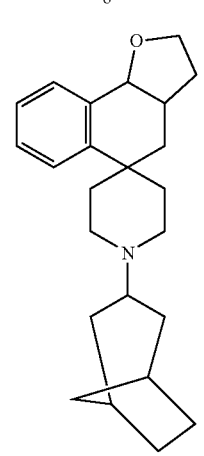
| 9 | 10 | 13 | 14 |
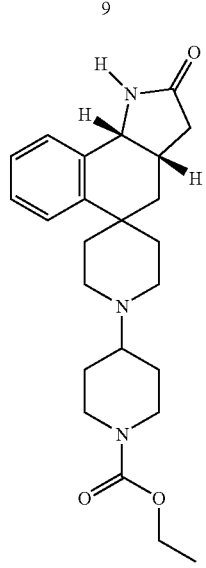 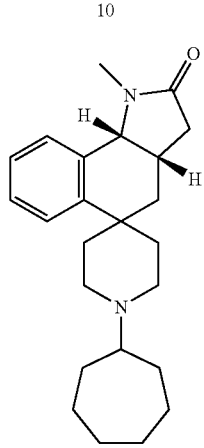 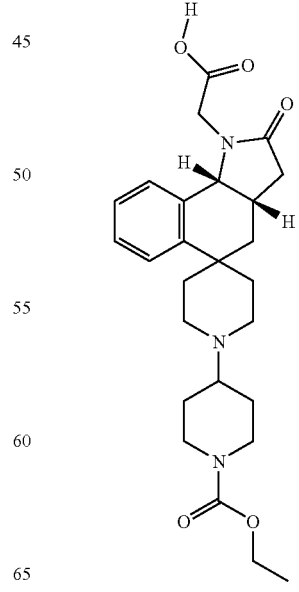 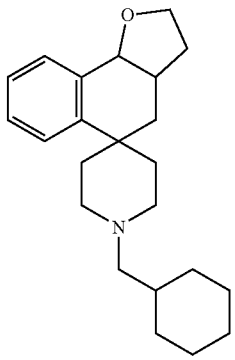

-continued
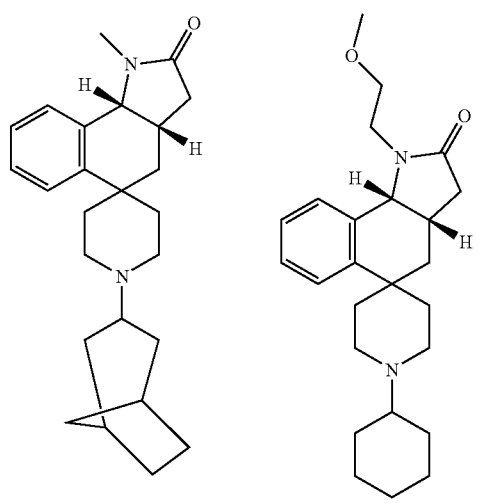
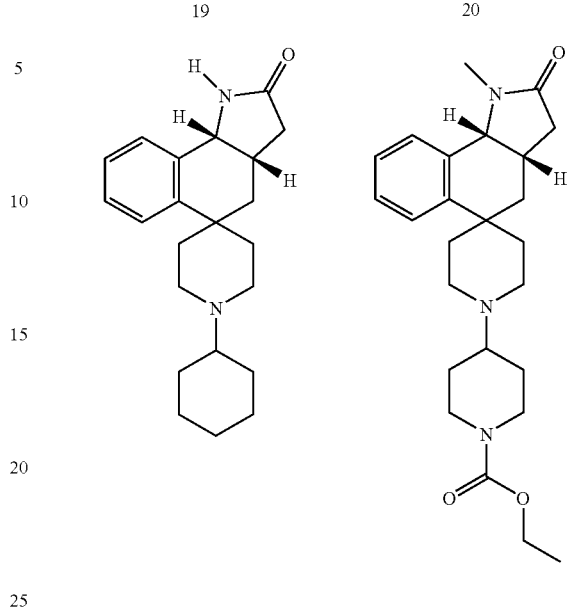
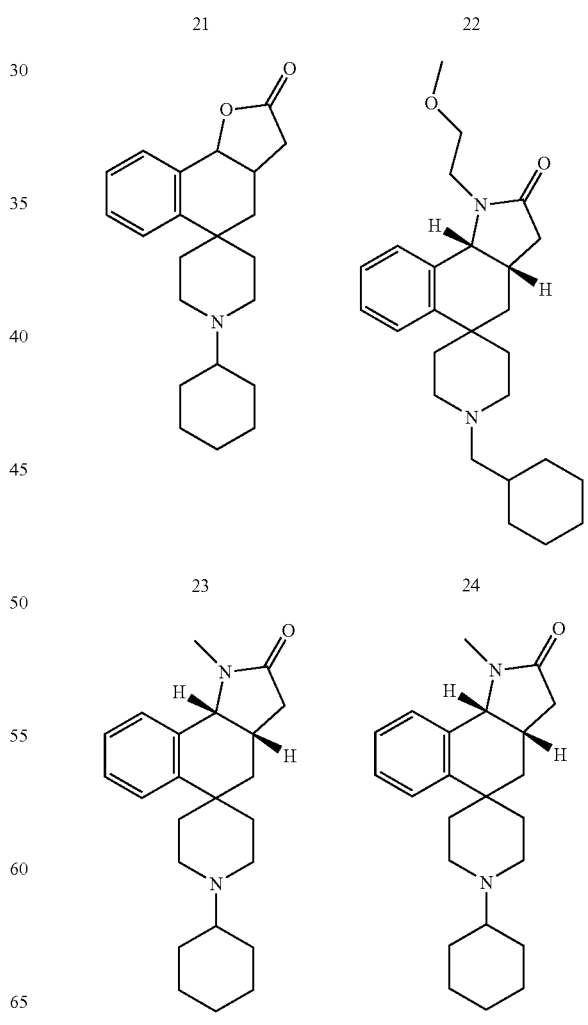

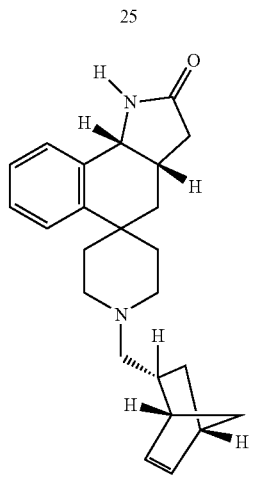
25
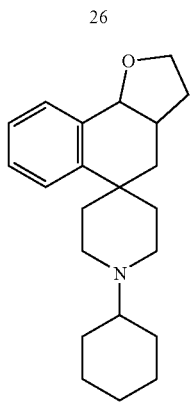
26
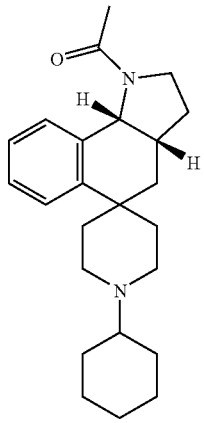
27
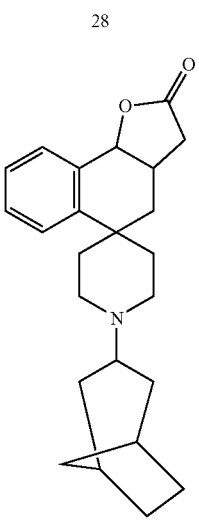
28
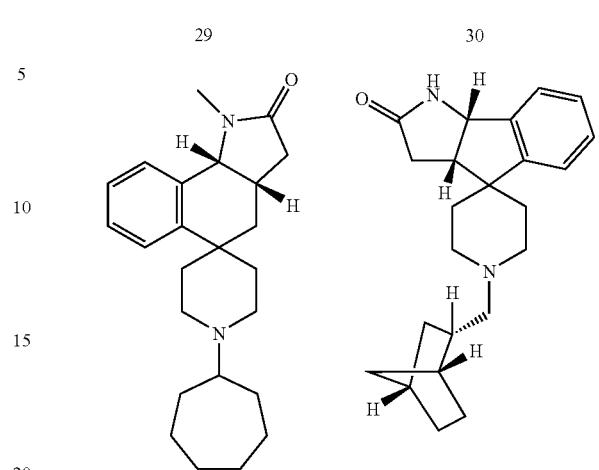
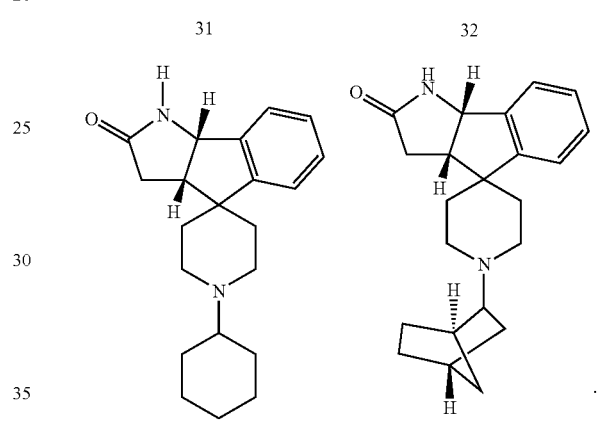
25. A pharmaceutical composition comprising a compound according to claim 24 and a pharmaceutical carrier.
* * * * *